United States Patent
Xu et al.

(10) Patent No.: US 7,677,101 B2
(45) Date of Patent: Mar. 16, 2010

(54) ESTIMATING PROPAGATION VELOCITY THROUGH A SURFACE ACOUSTIC WAVE SENSOR

(75) Inventors: Wenyuan Xu, Oakdale, MN (US); John S. Huizinga, Dellwood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/596,674

(22) PCT Filed: Dec. 17, 2004

(86) PCT No.: PCT/US2004/042793

§ 371 (c)(1),
(2), (4) Date: Jun. 21, 2006

(87) PCT Pub. No.: WO2005/066622

PCT Pub. Date: Jul. 21, 2005

(65) Prior Publication Data

US 2007/0068256 A1 Mar. 29, 2007

Related U.S. Application Data

(60) Provisional application No. 60/533,177, filed on Dec. 30, 2003.

(51) Int. Cl.
*G01N 29/024* (2006.01)
(52) U.S. Cl. .......................... 73/597; 73/61.79
(58) Field of Classification Search ........... 73/597–598, 73/54.41, 61.49, 61.79
See application file for complete search history.

(56) References Cited

U.S. PATENT DOCUMENTS

| | | | | |
|---|---|---|---|---|
| 4,730,494 A | * | 3/1988 | Ishikawa et al. | 73/606 |
| 5,012,668 A | | 5/1991 | Haworth | |
| 5,992,215 A | * | 11/1999 | Caron et al. | 73/24.01 |
| 6,062,091 A | | 5/2000 | Baumoel | |
| 2004/0265492 A1 | | 12/2004 | Free et al. | |
| 2005/0106709 A1 | | 5/2005 | Benson et al. | |
| 2005/0107615 A1 | | 5/2005 | Benson et al. | |
| 2005/0112672 A1 | | 5/2005 | Benson et al. | |
| 2005/0142296 A1 | | 6/2005 | Lakshmi | |
| 2005/0153370 A1 | | 7/2005 | Lakshmi et al. | |
| 2005/0212621 A1 | * | 9/2005 | Takamine | 333/195 |
| 2005/0227076 A1 | | 10/2005 | Benson et al. | |
| 2006/0019330 A1 | | 1/2006 | Lakshmi et al. | |
| 2006/0135718 A1 | | 6/2006 | Benson et al. | |

(Continued)

FOREIGN PATENT DOCUMENTS

JP 09325134 A * 12/1997

(Continued)

*Primary Examiner*—Hezron Williams
*Assistant Examiner*—Nashmiya S Fayyaz
(74) *Attorney, Agent, or Firm*—James A. Baker; Douglas B. Little

(57) ABSTRACT

Techniques are described for estimating the propagation velocity through a surface acoustic wave sensor. In particular, techniques which measure and exploit a proper segment of phase frequency response of the surface acoustic wave sensor are described for use as a basis of bacterial detection by the sensor. As described, use of velocity estimation based on a proper segment of phase frequency response has advantages over conventional techniques that use phase shift as the basis for detection.

19 Claims, 19 Drawing Sheets

U.S. PATENT DOCUMENTS

2006/0135783 A1 6/2006 Benson et al.

FOREIGN PATENT DOCUMENTS

| WO | WO 2005/064349 A2 | 7/2005 |
| WO | WO 2005/066092 A2 | 7/2005 |
| WO | WO 2005/066621 A1 | 7/2005 |
| WO | WO 2005/075973 A2 | 8/2005 |

* cited by examiner

Bacteria Concentration = 10³ Units

Bacteria Concentration = 10³ Units

Bacteria Concentration = 10⁵ Units

Bacteria Concentration = 10⁵ Units

Bacteria Concentration = 10⁷ Units

Bacteria Concentration = 10⁷ Units

ESTIMATING PROPAGATION VELOCITY THROUGH A SURFACE ACOUSTIC WAVE SENSOR

CROSS-REFERENCE TO RELATED APPLICATIONS

This application claims priority to U.S. Provisional Patent Application No. 60/533,177, filed Dec. 30, 2003.

This invention was made under a CRADA (SC02/01645) between Minnesota Mining and Manufacturing Company and Sandia National Laboratories, operated for the United State Department of Energy. The Government has certain rights in this invention.

TECHNICAL FIELD

The invention relates to surface acoustic wave (SAW) sensors and, more particularly, techniques for analyzing and interpreting the output of a SAW sensor.

BACKGROUND

Chemical and biological testing is commonly used to test for the presence or absence of chemical or biological agents. Testing for the presence of chemical or biological agents in blood, food or other materials is often performed to ensure safety or to facilitate diagnosis of medical conditions. For example, testing is used to identify chemicals, bacteria or other agents in blood samples taken from medical patients, laboratory samples developed for experimental purposes, food samples, or the like. In addition, chemical and biological testing is used to test for medical conditions such as pregnancy, diabetes, bacterial infection, and a wide variety of other conditions that may affect the patient's chemistry or biology.

One type of sensor that has been developed for chemical or biological sensing capabilities is a surface acoustic wave (SAW) sensor. One example of a SAW sensor is a Love mode shear-horizontal surface acoustic wave (SH-SAW) sensor. A SH-SAW sensor includes four main components: 1) a piezoelectric substrate; 2) an input inter-digitated transducer (IDT) on the substrate, which is used to excite an acoustic wave based on the piezoelectric effect; 3) an output IDT on the substrate, which receives the transmitted acoustic wave and generates electrical output by exploiting the piezoelectric effect; and 4) a wave-guide layer over the IDT's, which converts SH-type waves into waveguide Love modes for transmission from the input IDT to the output IDT. The presence of one or more materials on the surface of the SH-SAW sensor affects wave propagation through the waveguide layer in response to the presence of bacteria or other agents on the surface of the sensor, which facilitates detection of bacteria or other agents.

SUMMARY

In general, techniques are described for estimating the propagation velocity, or equivalently, for estimating a time delay through a surface acoustic wave sensor. In particular, techniques which measure and exploit a proper segment of phase frequency response of the surface acoustic wave sensor are described for use as a basis of bacterial detection by the sensor.

In one embodiment, the invention provides a method comprising identifying a segment of phase frequency response of a surface acoustic wave sensor, and estimating a time delay associated with wave propagation through the surface acoustic wave sensor based on the identified frequency response.

In another embodiment, the invention provides a computer-readable comprising instructions that when executed in a processor identify a segment of phase frequency response of a surface acoustic wave sensor, and estimate a time delay associated with wave propagation through the surface acoustic wave sensor based on the identified frequency response.

In another embodiment, the invention provides a system comprising a surface acoustic wave sensor, a sensor analyzer to receive output of the surface acoustic wave sensor, and a processor to receive input from the sensor analyzer, identify a segment of phase frequency response of a surface acoustic wave sensor, and estimate a time delay associated with wave propagation through the surface acoustic wave sensor based on the identified segment of phase frequency response.

The invention may be capable of providing one or more advantages. In particular, use of change of propagation velocity of a surface acoustic wave sensor, as described herein, can improve detection of bacteria via the sensor, relative to conventional techniques that use phase shift as the basis for detection. Moreover, use of an estimated propagation velocity of a surface acoustic wave sensor as the basis for detection may allow for detection of bacterial concentration.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
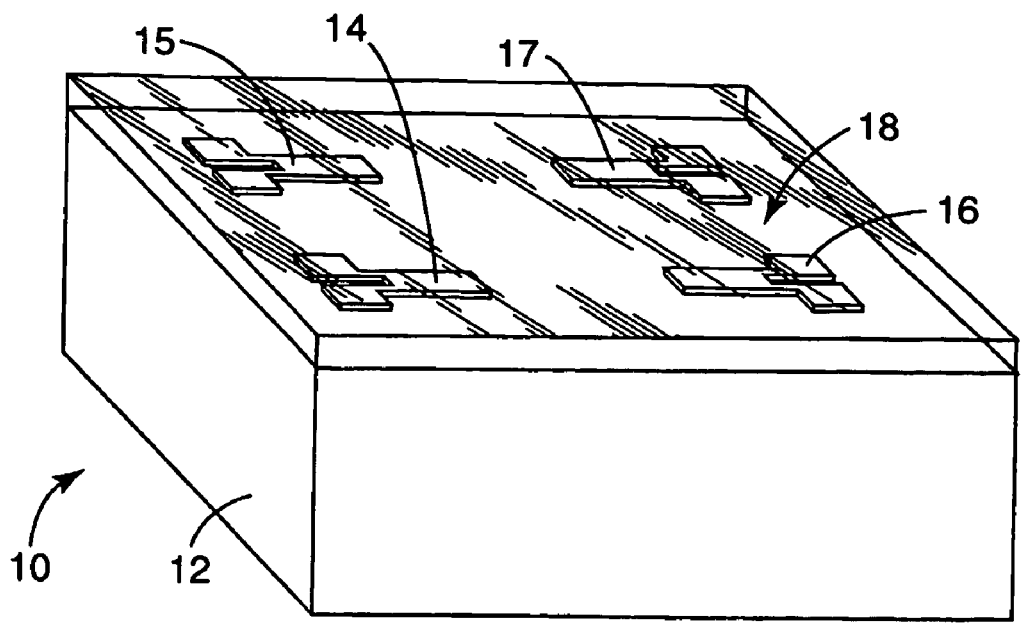
FIG. 1 is a perspective view illustrating an exemplary surface acoustic wave (SAW) sensor that may be used in one or more embodiments of the invention.

FIG. 1 is a perspective view illustrating an exemplary SAW sensor 10 that may be used in accordance with an embodiment of the invention. SAW sensor 10 may comprise any of a wide variety of SAW sensors. SH-SAW sensors are typically constructed from a piezoelectric material with a crystal-cut and orientation that allows the wave propagation to be rotated to a shear horizontal mode, i.e., parallel to the plane defined by the waveguide, resulting in reduced acoustic damping loss to a liquid in contact with the detection surface. Shear horizontal acoustic waves may include, e.g., thickness shear modes (TSM), acoustic plate modes (APM), surface skimming bulk waves (SSBW), Love-waves, leaky acoustic waves (LSAW), and Bleustein-Gulyaev (BG) waves.

In particular, Love wave sensors may include a substrate supporting a SH wave mode such as SSBW of ST quartz or the leaky wave of 36°YXLiTaO$_3$. These modes may preferably be converted into a Love-wave mode by application of thin acoustic guiding layer or waveguide. These waves are frequency dependent and can be generated if the shear wave velocity of the waveguide layer is lower than that of the piezoelectric substrate.

In one example, sensor 10 comprises a Love mode shear-horizontal surface acoustic wave (SH-SAW) sensor.

SAW sensor 10 includes a substrate 12 which typically comprises a piezoelectric material. SAW sensor 10 also includes an input inter-digital transducer (IDT) 14 on substrate 12, which is used to excite an acoustic wave based on the piezoelectric effect. In addition, SAW sensor 10 includes an output IDT 16 on substrate 12, which receives the transmitted acoustic wave and generates electrical output by exploiting the piezoelectric effect. A wave-guide layer 18 is formed over the IDT's 14, 16. Wave-guide layer 18 converts SH-type waves into waveguide Love modes for transmission from input IDT 14 to output IDT 16.

A layer of material, such as a layer of antibodies is applied over waveguide layer 18. In operation, a fluid being tested for the presence of bacteria is brought into contact with waveguide layer 18. If bacteria is present in the fluid, the bacteria attaches to the antibodies on waveguide layer 18 and thereby affect wave propagation through waveguide layer 18. Accordingly, analysis of the wave propagation through waveguide layer 18 of SAW sensor 10 allows for bacterial detection or detection of other agents that may interact with a material coated on waveguide layer 18.

In some cases, SAW sensor 10 includes a plurality of sets of input and output IDT's. For example, SAW sensor 10 may include a first input IDT 14 and a second input IDT 15 which respectively correspond to first output IDT 16 and second output IDT 17. In that case, first input and output IDT's 14, 16 comprise the active portion of SAW sensor 10, and second input and output IDT's 15, 17 comprise the reference portion of SAW sensor 10. Different types of antibodies may be coated on the surface of waveguide layer 18 between first input and output IDT's 14, 16 and second input and output IDT's 15, 17, such that only the bacteria of interest bonds to the antibodies between the active portion corresponding to first input and output IDT's 14, 16. In that case, the reference portion corresponding to second input and output IDT's 15, 17 allows for reference measurements which can account for temperature variance affects, or the like, which could otherwise affect wave propagation through SAW sensor 10.

SAW sensors are commonly used for bacterial detection but may be designed for detection of any of a wide variety of other chemical or biological agents. Accordingly, different materials may be coated on the waveguide layer of SAW sensor 10 in order to facilitate detection of various chemical or biological agents. Waveguide materials may preferably be materials that exhibit one or more of the following properties: low acoustic losses, low electrical conductivity, robustness and stability in water and aqueous solutions, relatively low acoustic velocities, hydrophobicity, higher molecular weights, highly cross-linked, etc. In one example, $SiO_2$ has been used as an acoustic waveguide layer on a quartz substrate. Examples of other thermoplastic and crosslinked polymeric waveguide materials include, e.g., epoxy, polymethylmethacrylate, phenolic resin (e.g., NOVALAC), polyimide, polystyrene, etc.

In general, the presence of a particular material on the surface of the SAW sensor affects wave propagation through the waveguide layer in response to the presence or absence of another material passing over the waveguide layer, which facilitates detection of the material passing over the waveguide layer. Accordingly, materials coated on the waveguide layer may be selected to attract, trap, bond with or otherwise attach to materials suspended in a fluid that flows across waveguide layer 18. In this manner, SAW sensor 10 facilitates detection of bacteria or other biological or chemical agents.

In order to generate Love mode surface wave, the shear wave velocity of waveguide layer 18 is typically lower than that of substrate 12. In that case, the acoustic energy will be trapped to near the sensing surface of SAW sensor 10. Love mode SH-SAW sensors, in particular, generally have high sensitivity to surface perturbations. Mass loading can change the surface conditions of a Love mode SH-SAW sensor. Therefore, measuring the change of the propagation velocity or resonant frequency can be used to quantitatively detect mass loading, and thereby detect the presence of a chemical or biological agent.

One of the most important performance indices for an SH-SAW sensor used as a detector is the mass sensitivity, i.e., how sensitive is the sensor to the loading mass on its surface. For analyzing the mass sensitivity, two indices have been established:

$$s_m^v = \frac{1}{v_0} \lim_{\Delta m_s \to 0} \frac{\Delta v}{\Delta m_s} \text{ and } s_m^f = \frac{1}{f_0} \lim_{\Delta m_s \to 0} \frac{\Delta f}{\Delta m_s},$$

where $\frac{\Delta v}{v_0} = \frac{v_1 - v_0}{v_0}$ and $\frac{\Delta f}{f_0} = \frac{f_{resonance}^{(1)} - f_{resonance}^{(0)}}{f_{resonance}^{(0)}} \cdot v_0$, $f_{resonance}^{(0)}$ and $v_1, f_{resonance}^{(1)}$ the propagation velocities and resonant frequencies of the sensor without and with surface perturbation resulting from an infinitesimal thin rigid loading layer with mass $\Delta m_s = \rho_m \epsilon$, where $\rho_m$ and $\epsilon$ are the density and thickness of the loading layer.

$$s_m^v \approx \frac{v_0}{v_g} s_m^f,$$

where $v_g$ is the group velocity, and for Love mode SH-SAW $$\frac{v_0(\omega)}{v_g(\omega)} > 1,$$

where the notation $v_0(\omega)$ as well as $v_g(\omega)$ is used to emphasize that the velocities are frequency dependent in the dispersive cases. This means that for Love mode SH-SAW sensor, using $\Delta v/v_0$ for detecting the anomalies of the boundary conditions of the surface of the sensor should be better than using $\Delta f/f_0$. Accordingly, in accordance with the invention, $\Delta v/v_0$ may be used as a basis of a detection indicator for SAW-sensor 10, or the like.

Conventionally, for a Love mode SH-SAW sensor with a triple transit echo (TTE), the phase frequency response was given by:

$$\varphi(\omega) = -\frac{1+\beta}{1-\beta} \frac{L\omega}{v(\omega)},$$

or equivalently:

$$\varphi(f) = -\frac{1+\beta}{1-\beta}\frac{2\pi L f}{v(f)},$$

where f and ω represent frequency and angular frequency, L is the distance between the center of the input and center of the output IDT, $\beta=\alpha^2$ and α is the reflection coefficient of the input and output IDTs. Since β is small and can be determined by frequency response, without loss of generality, β is assumed to be zero. Thus, for phase frequency response, one only needs to be concerned with the case that does not include TTE. The phase frequency response is therefore:

$$\varphi(\omega) = -\frac{L\omega}{v(\omega)} \text{ or } \varphi(f) = -\frac{2\pi L f}{v(f)} = -2\pi f \tau(f).$$

However, $e^{j\phi(f)}=e^{-j2\pi f\tau(f)}=e^{-j2\pi(f\tau(f)+k)}$, where k=0, ±1, ±2, ±3, etc. Thus, the phase frequency response φ(f) is multi-valued and cannot be uniquely determined by the value of $e^{j\phi(f)}$. This problem is called phase ambiguity. Only a so-called "main value" of φ(f) can be determined from $e^{j\phi(f)}$. Since $$\exp\{-j2\pi f\tau(f)\}=\exp\{-j2\pi(f\tau(f)-[f\tau(f)])\},$$

where [x] is the integer part of x, i.e. [x] is the maximum of the integers, which are less or equal to x, the main value of the phase response becomes:

φ(f)=−2π(fτ(f)−[fτ(f)])+π (in radian) or φ(f)=−360(fτ(f)−[fτ(f)])+180 (in degree).

Thus, −π<φ(f)≦π (in radian) or −180<φ(f)≦180 (in degree).

For $$\varphi(f) = -2\pi f \frac{L}{v},$$

$$\left.\frac{d\varphi}{dv}\right|_{v=v_0} = 2\pi f \frac{L}{v_0^2}.$$

Therefore, an approximation of the phase change is given by:

$$\Delta\varphi = 2\pi f \frac{L}{v_0^2}\Delta v.$$

Therefore, $$\frac{\Delta\varphi}{\varphi_0} = \frac{2\pi f \frac{L}{v_0^2}\Delta v}{-2\pi f \frac{L}{v_0}} = -\frac{\Delta v}{v_0}.$$

Unfortunately, however, this derivation does not hold for $$\phi(f) = -2\pi\left(f\frac{L}{v} - \left[f\frac{L}{v}\right]\right) + \pi.$$

If $\left[f\frac{L}{v_0}\right] = \left[f\frac{L}{v_0+\Delta v}\right]$, then $\frac{\Delta\phi}{\phi_0} = -\frac{\Delta v}{v_0}.$ Otherwise, $\frac{\Delta\phi}{\phi_0} = \frac{-\frac{L}{v_0^2}\Delta v + \left[f\frac{L}{v_0+\Delta v}\right] - \left[f\frac{L}{v_0}\right]}{-\frac{L}{v_0} + \left[f\frac{L}{v_0}\right]} \neq -\frac{\Delta v}{v_0}.$ The condition $$\left[f\frac{L}{v_0}\right] = \left[f\frac{L}{v_0+\Delta v}\right]$$

implies $$f\left|\frac{L}{v_0} - \frac{L}{v_0+\Delta v}\right| < 1. \text{ Let } f\left|\frac{L}{v_0} - \frac{L}{v_0+\Delta v}\right| = 1,$$

i.e.

$$f\left|\frac{L\Delta v}{v_0(v_0+\Delta v)}\right| = 1.$$

For Δv<0, it follows that:

$$\frac{\Delta v}{v_0(v_0+\Delta v)} = -\frac{1}{fL} \text{ and } \Delta v = -\frac{v_0^2}{fL+v_0}.$$

This means that when $$|\Delta v| \geq \frac{v_0^2}{fL+v_0}, \left[f\frac{L}{v_0}\right] \neq \left[f\frac{L}{v_0+\Delta v}\right].$$

For example, If f=103 MH, $v_0$=4000 m/s and L=8.8 mm, then $$\left[f\frac{L}{v_0}\right] \neq \left[f\frac{L}{v_0+\Delta v}\right]$$

for |Δv|≧17.5747 m/s. Therefore, when $$\left[f\frac{L}{v_0}\right] \neq \left[f\frac{L}{v_0+\Delta v}\right], \Delta\phi \text{ or } \frac{\Delta\phi}{\phi_0}$$

may not be a proper indicator function.

For this reason, the invention provides techniques for estimating the propagation velocity through a SAW sensor based on an identified segment of phase frequency response. The propagation velocity is simply related to the time delay through the SAW sensor, as described below. In accordance with the invention, a method may include identifying a proper segment of phase frequency response of a surface acoustic wave sensor, and estimating a time delay associated with wave propagation through the surface acoustic wave sensor based on the identified frequency response.

Figure 2:
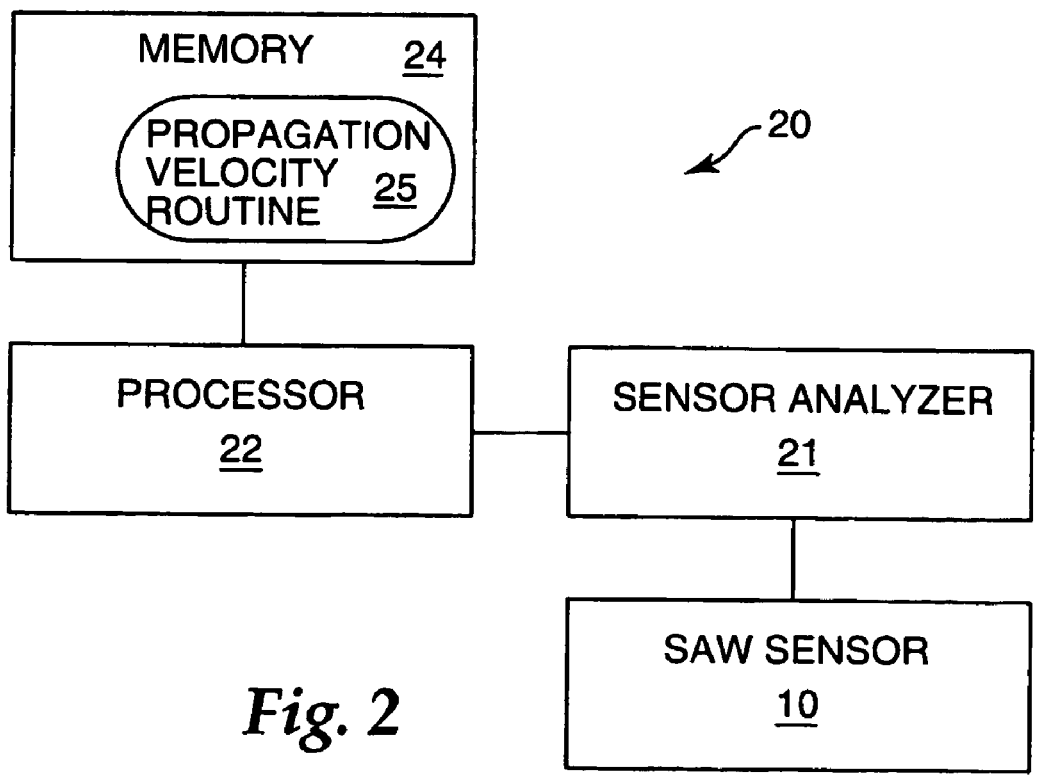
FIG. 2 is a block diagram illustrating a system according to an embodiment of the invention.

FIG. 2 is a block diagram illustrating a system 20 that includes a SAW sensor 10, and a sensor analyzer 21 that obtains measurements from SAW sensor 10. System 20 also includes a processor 22 that interprets the output of SAW sensor 10. In other words, sensor analyzer 21 receives output from SAW sensor 10 and provides input to processor 22 so that the output of SAW sensor 10 can be interpreted.

Processor 22 receives input from sensor analyzer 21, which comprises measurements associated with wave propagation through SAW sensor 10. Processor 22 then determines whether SAW sensor 10 has detected the presence of particular bacteria or other material for which SAW sensor 10 is designed to detect. Processor 22 executes instructions to perform various techniques and functions ascribed to the processor herein. Although the invention is not limited in this respect, SAW sensor 10 may be housed in a cartridge, or the like, and may be electrically coupled to sensor analyzer 21 via insertion of the cartridge into a slot. Processor 22 may be housed in the same unit as sensor analyzer 21 or may be part of a separate unit or separate computer.

Processor 22 may also be coupled to memory 24, which stores a propagation velocity routine 25 consistent with the teaching of this disclosure. Alternatively, propagation velocity routine 25 may be implemented by hardware within processor 22. In any case, processor 22 executes propagation velocity routine 25 in order to estimate a time delay associated with wave propagating through the surface acoustic wave sensor based on the identified frequency response, as described herein.

By way of example, processor 22 may comprise a general-purpose microprocessor that executes software stored in memory 24. In that case, processor 22 may be internally housed in a specifically designed computer, a general purpose personal computer, workstation, handheld computer, laptop computer, or the like. Alternatively, processor 22 may comprise an application specific integrated circuit (ASIC) or other specifically designed processor. In any case, processor 22 executes propagation velocity routine 25 in order to estimate a time delay associated with wave propagation through the surface acoustic wave sensor 10 based on the identified frequency response, as described herein.

Memory 24 is one example of a computer readable medium that stores processor executable software instructions applied by processor 22. By way of example, memory 24 may comprise random access memory (RAM), read-only memory (ROM), non-volatile random access memory (NVRAM), electrically erasable programmable read-only memory (EEPROM), flash memory, or the like. Propagation velocity routine 25 such as one of those mathematically described below, are stored in memory 24 and may form part of a larger software program used for analysis of the output of SAW sensor 10. For example, propagation velocity routine 25 may be a sub-routine programmed within a LabView software platform, which is described in greater detail below.

Figure 3:
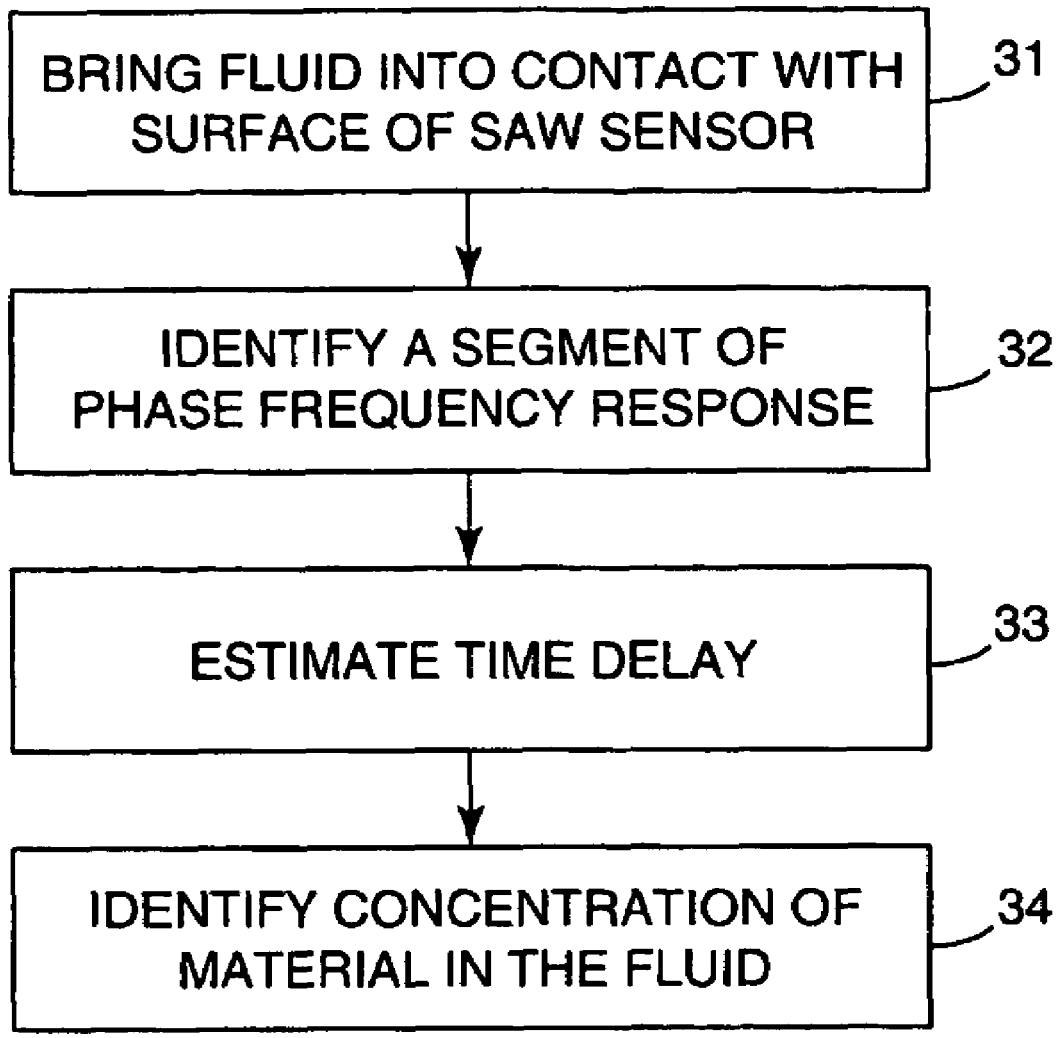
FIG. 3 is a flow diagram illustrating a technique according to an embodiment of the invention.

FIG. 3 is a flow diagram illustrating a technique according to an embodiment of the invention. As shown in FIG. 3, fluid is brought into contact with a surface of SAW sensor 10 (31). The fluid may include samples of material for which bacterial testing is needed. For example, the fluid may be allowed to pass over the surface of waveguide layer 18 of SAW sensor 10 (FIG. 1), which includes antibodies that react to the bacteria of interest. SAW sensor 10, for example, may be housed in a cartridge that defines a fluid path over the surface of waveguide layer 18 such that a fluid can be introduced into the cartridge and allowed to pass over waveguide layer 18 via the fluid path.

Processor 22 receives measurements taken from SAW sensor 10 by sensor analyzer 21, and applies propagation velocity routine 25 stored in memory 24. In doing so, processor 22 identifies a segment of phase frequency response of SAW sensor 10 (32), and estimates a time delay associated with wave propagation through SAW sensor 10 based on the identified frequency response (33). In some embodiments, an estimated propagation velocity derived from the estimated time delay can be used to identify the concentration of the bacteria or other material in the fluid (34).

Numerous mathematical techniques for estimating the time delay associated with wave propagation through the surface acoustic wave sensor will now be discussed.

$$\tau = \frac{L}{v}$$

refers to the time delay between the center of the input and the center of the output IDT separated by distance L. In the dispersive case, the time delay is also a function of the frequency. That is, $$\tau(f) = \frac{L}{v(f)}.$$

It follows from the definition of $\phi(f)$ (in degree) that:

$$f\tau(f) = [f\tau(f)] - \frac{\phi(f)}{360} + 0.5.$$

Figure 4:
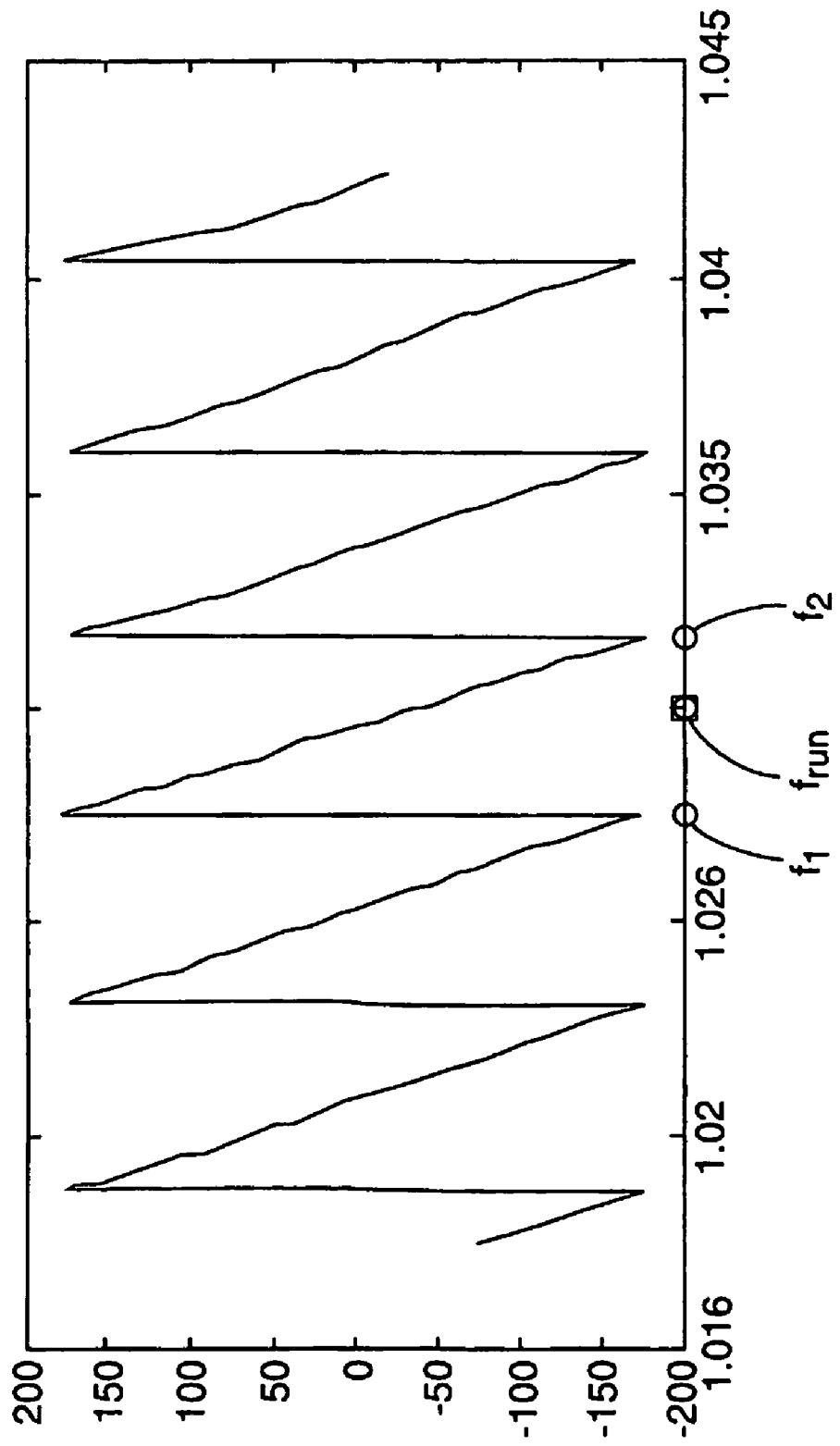
FIG. 4 is a graph illustrating an example phase frequency response of a SAW sensor.

For any given running frequency $f_0$ (also referred to as the operating frequency), there are two phase inflection frequencies $f_1$ and $f_2$ proximate to a running frequency $f_0$ such that:

(1) $f_1 \leq f_0 < f_2$ (2) $\phi(f_1)=180$, $\phi(f_2-0)=-180$ and $\phi(f_2)=\phi(f_2+0)=180$, (3) $f_1\tau(f_1)=[f_1\tau(f_1)]$, $f_2\tau(f_2)=[f_2\tau(f_2)]$ and $[f_2\tau(f_2)]=[f_1\tau(f_1)]+1$, and (4) For any $f_1 \leq f < f_2$, $[f\tau(f)]=[f_1\tau(f_1)]$, FIG. 4 is a graph illustrating an example frequency response of a SAW sensor. Labeled in FIG. 4 is an exemplary a running frequency $f_0$, a typical first phase inflection frequency $f_1$ and a typical second phase inflection frequency $f_2$. Again, for any $f_1 \leq f < f_2$, $[f\tau(f)]=[f_1\tau(f_1)]$. Therefore:

$$f\tau(f) = [f_1\tau(f_1)] - \frac{\phi(f)}{360} + 0.5, \text{ for } f_1 \leq f \leq f_2.$$

Taking the derivative with respect to f for both sides of the above equality, results in:

$$f\frac{d\tau(f)}{df} + \tau(f) = -\frac{1}{360}\frac{d\phi(f)}{df}, \text{ for } f_1 \leq f < f_2.$$

That is,

-continued
$$\frac{d\tau(f)}{df} + \frac{1}{f}\tau(f) = \frac{1}{360}\frac{1}{f}\frac{d\phi(f)}{df}, \text{ for } f_1 \le f < f_2,$$

which is one basic differential equation for calculating the time delay $\tau(f)$.

If the initial condition is: $\tau(f)|_{f=f_{00}} = \tau(f_{00})$, where $f_{00} \in [f_1, f_2)$ and arbitrary, then the solution of the basic differential equation for calculating the time delay $\tau(f)$ becomes:

$$\tau(f) = \frac{f_{00}}{f}\tau(f_{00}) - \frac{1}{360}\frac{1}{f}\phi(f) + \frac{1}{360}\frac{1}{f}\phi(f_{00}).$$

The solution can be easily derived from:

$$f\tau(f) = [f_1\tau(f_1)] - \frac{\phi(f)}{360} + 0.5$$

and $$f_{00}\tau(f_{00}) = [f_1\tau(f_1)] - \frac{\phi(f_{00})}{360} + 0.5.$$

The basic differential equation may be used to prove the following properties of $\tau(f)$.

Proposition 1: If for $f \in [f_{11}, f_{22}] \subseteq [f_1, f_2)$, $\phi(f)$ is linear with respect to $f$, then $\tau(f)$ is constant and $$\tau(f) = -\frac{1}{360}\frac{\phi(f_{22}) - \phi(f_{11})}{f_{22} - f_{11}}, \text{ for } f \in [f_{11}, f_{22}] \subseteq [f_1, f_2).$$

Proof of Proposition 1:

Suppose $$f_{00} \in [f_{11}, f_{22}] \cdot \tau(f) = -\frac{1}{360}\dot{\phi}(f_{00})$$

is the solution of the basic differential equation:

$$f\frac{d\tau(f)}{df} + \tau(f) = -\frac{1}{360}\frac{d\phi(f)}{df},$$

in $[f_{11}, f_{22}]$ because the left side $$f\frac{d\tau(f)}{df} + \tau(f) = \tau(f) = -\frac{1}{360}\dot{\phi}(f_{00})$$

and the right side $$-\frac{1}{360}\frac{d\phi(f)}{df} = -\frac{1}{360}\dot{\phi}(f_{00})$$

due to the linearity of $\phi(f)$ in $[f_{11}, f_{22}]$. It is also from the linearity of $\phi(f)$ in $[f_{11}, f_{22}]$ that $$\dot{\phi}(f_{00}) = \frac{\phi(f_{22}) - \phi(f_{11})}{f_{22} - f_{11}}.$$

Proposition 2: Suppose $\phi(f)$ is differentiable in $(f_1, f_2)$ and right differentiable for $f_1$. Then:

$$\hat{\tau}(f) = -\frac{1}{360}\frac{d\phi(f)}{df}$$

is the first order estimation of $\tau(f)$.

Proof or Proposition 2:

In the neighborhood of $f_{00} \in [f_1, f_2)$, $$\phi(f) \approx \phi(f_{00}) + \dot{\phi}(f_{00})(f - f_{00}).$$

Therefore, in this neighborhood $\phi(f)$ is approximately linear with respect to $f$ and $\dot{\phi}(f) \approx \dot{\phi}(f_{00})$. From the proposition 1, $$\tau(f) = -\frac{1}{360}\frac{d\phi(f)}{df}.$$

That is, $$\hat{\tau}(f) = -\frac{1}{360}\frac{d\phi(f)}{df}$$

is the first order of estimation of $\tau(f)$.

Algorithms or routines for estimating the Time Delay $\tau(f)$ will now be discussed. From proposition 2, the following algorithms can be used as part of propagation velocity routine 25 to obtain the estimate of $\tau(f)$.

Algorithm 1:

$$f_{00} = f_1 \text{ and } \hat{\tau}(f_1) = -\frac{1}{360}\dot{\phi}(f_1)$$
$$\approx -\frac{1}{360}\frac{\phi(f_2) - \phi(f_1)}{f_2 - f_1} \approx \frac{1}{f_2 - f_1}.$$

Using the equation:

$$\tau(f) = \frac{f_{00}}{f}\tau(f_{00}) - \frac{1}{360}\frac{1}{f}\phi(f) + \frac{1}{360}\frac{1}{f}\phi(f_{00}),$$

one obtains:

$$\hat{\tau}(f) = \frac{f_1}{f}\frac{1}{f_2 - f_1} - \frac{1}{360}\frac{\phi(f)}{f} + \frac{0.5}{f}.$$

In particular:

$$\hat{\tau}(f_0) = \frac{f_1}{f_0} \frac{1}{f_2 - f_1} - \frac{1}{360} \frac{\phi(f_0)}{f_0} + \frac{0.5}{f_0},$$

where $f_0$ is running frequency and is also denoted by $f_{run}$ in this description.

Algorithm 2: $f_{00} = f_*$, e.g. $\phi(f_*) = \pm 90$. Around $f_*$ take 10 frequencies $f^{(1)}, f^{(2)}, \ldots, f^{(10)}$ and a linear regression for $(f^{(1)}, \phi(f^{(1)})), (f^{(2)}, \phi(f^{(2)})), \ldots, (f^{(10)}, \phi(f^{(10)}))$.

The slope of this line is denoted by $$\dot{\phi}(f_*) \text{ and } \hat{\tau}(f_*) = -\frac{1}{360} \dot{\phi}(f_*).$$

Therefore, $$\hat{\tau}(f) = -\frac{1}{360} \frac{f_*}{f} \dot{\phi}(f_*) - \frac{1}{360} \frac{1}{f} \phi(f) + \frac{1}{360} \frac{1}{f} \phi(f_*)$$

Algorithm 3: $f_{00} = f_0 = f_{run}$. Around $f_0$ take 10 frequencies $f^{(1)}, f^{(2)}, \ldots, f^{(10)}$ and a linear regression for $(f^{(1)}, \phi(f^{(1)})), (f^{(2)}, \phi(f^{(2)})), \ldots, (f^{(10)}, \phi(f^{(10)}))$. The slope of this line is $\dot{\phi}(f_0)$ and the first order estimation of $\tau(f_0)$ is $$\hat{\tau}(f_0) = -\frac{1}{360} \dot{\phi}(f_0).$$

Algorithm 4: Since $$\tau(f) \approx \frac{f_{00}}{f} \hat{\tau}(f_{00}) - \frac{1}{360} \frac{1}{f} \phi(f) + \frac{1}{360} \frac{1}{f} \phi(f_{00})$$

$$= -\frac{1}{360} \frac{f_{00}}{f} \dot{\phi}(f_{00}) - \frac{1}{360} \frac{1}{f} \phi(f) + \frac{1}{360} \frac{1}{f} \phi(f_{00})$$

holds for any $f_{00} \in [f_1, f_2)$. Regarding $f_{00}$ as a variable and taking integral with respect to $f_{00}$ for both sides of the above approximate equation, provides $$\int_{f_1}^{f_2} \tau(f) df_{00} \approx -\frac{1}{360} \frac{1}{f} \int_{f_1}^{f_2} f_{00} \dot{\phi}(f_{00}) df_{00} -$$
$$\frac{1}{360} \int_{f_1}^{f_2} \frac{1}{f} \phi(f) df_{00} + \frac{1}{360} \int_{f_1}^{f_2} \frac{1}{f} \phi(f_{00}) df_{00},$$

which is equivalent to $$\tau(f)(f_2 - f_1) \approx -\frac{1}{360} \frac{1}{f} \left( f_2 \phi(f_2) - f_1 \phi(f_1) - \int_{f_1}^{f_2} \phi(f_{00}) df_{00} \right) -$$
$$\frac{1}{360} \frac{1}{f} \phi(f)(f_2 - f_1) + \frac{1}{360} \int_{f_1}^{f_2} \frac{1}{f} \phi(f_{00}) df_{00},$$

i.e., $$\tau(f) \approx -\frac{1}{360} \frac{1}{f} \frac{f_2 \phi(f_2) - f_1 \phi(f_1)}{f_2 - f_1} -$$
$$\frac{1}{360} \frac{1}{f} \phi(f) + \frac{2}{360} \frac{1}{f} \frac{1}{f_2 - f_1} \int_{f_1}^{f_2} \phi(f_{00}) df_{00}.$$

Because $\phi(f_1) = 180$, $\phi(f_2 - 0) = -180$, $$\hat{\tau}(f) \approx \frac{1}{2} \frac{1}{f} \frac{f_2 + f_1}{f_2 - f_1} - \frac{1}{360} \frac{1}{f} \phi(f) + \frac{2}{360} \frac{1}{f} \frac{1}{f_2 - f_1} \int_{f_1}^{f_2} \phi(f_{00}) df_{00}$$

$$= \frac{1}{2} \frac{1}{f} \frac{f_2 - f_1 + 2f_1}{f_2 - f_1} - \frac{1}{360} \frac{1}{f} \phi(f) + \frac{2}{360} \frac{1}{f} \frac{1}{f_2 - f_1} \int_{f_1}^{f_2} \phi(f_{00}) df_{00}$$

$$= \frac{1}{f} \frac{f_1}{f_2 - f_1} - \frac{1}{360} \frac{1}{f} \phi(f) + \frac{0.5}{f} + \frac{1}{180} \frac{1}{f} \frac{1}{f_2 - f_1} \int_{f_1}^{f_2} \phi(f_{00}) df_{00}.$$

In particular, $$\hat{\tau}(f_0) =$$
$$\frac{1}{f_0} \frac{f_1}{f_2 - f_1} - \frac{1}{360} \frac{1}{f_0} \phi(f_0) + \frac{0.5}{f_0} + \frac{1}{180} \frac{1}{f_0} \frac{1}{f_2 - f_1} \int_{f_1}^{f_2} \phi(f_{00}) df_{00}.$$

Comparing the $\hat{\tau}(f)$ in algorithm 1 with that of algorithm 4, shows that algorithm 4 adds one more term $$\frac{1}{180} \frac{1}{f} \frac{1}{f_2 - f_1} \int_{f_1}^{f_2} \phi(f_{00}) df_{00}.$$

If the phase function $\phi(f)$ is symmetric about the point $((f_1 + f_2)/2, 0)$, then $$\int_{f_1}^{f_2} \phi(f_{00}) df_{00} = 0.$$

In that case, algorithms 1 and 4 are the same. This means that the term $$\frac{1}{180} \frac{1}{f} \frac{1}{f_2 - f_1} \int_{f_1}^{f_2} \phi(f_{00}) df_{00}$$

is used to reduce the estimation error of the algorithm 1 resulting from non-symmetry of the phase response $\phi(f)$.

For the real measured phase response, $\phi(f)$ is only given at the sampling points of the frequency f. That is, $\phi(f)$ is a discrete sequence rather than a continuous function in the interval $[f_1, f_2)$. Furthermore, $\phi(f_1)$ and $\phi(f_2)$ may be not equal to 180 and −180, respectively, although it is true that $\phi(f_1 - \Delta f) < 0$, $\phi(f_1) > 0$, $\phi(f_2) < 0$ and $\phi(f_2 + \Delta f) > 0$, where $\Delta f$ is the sampling interval in the frequency domain. In order to increase the estimation accuracy, $\Delta f$ should be as small as possible and linear regression can be used to extrapolate $\phi(f)$ from $[f_1, f_2)$ to

[$f_{new1}, f_{new2}$) such that $\phi(f_{new1})=180$ and $\phi(f_{new2}-0)=-180$. For the extrapolated $\phi(f)$, $$\hat{\tau}(f_0) = \frac{1}{f_0} \frac{f_{new1}}{f_{new2} - f_{new1}} - \frac{1}{360} \frac{1}{f_0} \phi(f_0) +$$

$$\frac{0.5}{f_0} + \frac{1}{180} \frac{1}{f_0} \frac{\Delta f}{f_{new2} - f_{new1}} \sum_{f_{new1}}^{f_{new2}} \phi(f_{00})$$

or simply $$\hat{\tau}(f_0) = \frac{1}{f_0} \frac{f_{new1}}{f_{new2} - f_{new1}} - \frac{1}{360} \frac{1}{f_0} \phi(f_0) + \frac{0.5}{f_0}.$$

Notably, the above algorithms for estimating the propagation velocity are only based on a proper segment of the measured frequency response of the SH-SAW sensor. In at least this way, the algorithms are different than conventional methods. Conventional methods, may measure the time delay of the sensor or time delays between several fingers of IDT by some time domain device. Alternatively, conventional methods may be based on an entire phase frequency response, an amplitude frequency response, and an inverse Fourier transform. In contrast, the techniques described herein are based only on a segment of the measured frequency response of the SH-SAW sensor, i.e., the proper segment, which can be identified as described herein.

Algorithm 1 was implemented in the software platform LabView for on-line velocity measurement. LabView is a commercially available software program that can be obtained from National Instruments, Inc., USA. Using a SAW sensor as a detector is generally based on the comparison of propagation characteristics of the sensor without and with a particular surface perturbation. Such a comparison can be carried out dynamically or statically.

For the dynamic comparison, the propagation characteristic of the sensor is measured as a time series. For the static comparison, the sensor should consist of two channels, the reference channel and detection channel (also called the active channel). For example, the reference channel may correspond to the reference portion between IDTs 15 and 17 (FIG. 1), whereas the detection channel may correspond to the active portion between DITs 14 and 16. The surface perturbation takes place in the detection channel. In that case, the propagation characteristics of two channels of the sensor are measured. The measurement of propagation characteristic of SH-SAW sensor is the base for using the sensor as a detector.

Resonance frequency $f_{resonance}$ and propagation velocity v are two of the most direct propagation characteristics, and $\Delta v/v$ are more sensitive than $\Delta f/f$ to the surface perturbation. Therefore, the measurement of the propagation velocity may provide an improved method for efficiently using SH-SAW sensor as a detector. In contrast, conventional techniques typically measure the log-amplitude response A(f) and phase response $\phi(f)$ of SH-SAW sensor by a sensor analyzer and read out the phase at the running frequency from the measured phase frequency response. Developing routines for the direct measurement of the propagation velocity of the SH-SAW sensor becomes very important in the practical application of SH-SAW sensor. The algorithms presented above provide a software-based approach to estimate the propagation velocity from a proper segment of the measured phase frequency response, e.g., which can be measured by an 8753ET network analyzer commercially available from Agilent Technologies, Inc., USA. Other similar network analyzers could also be used.

Figure 5:
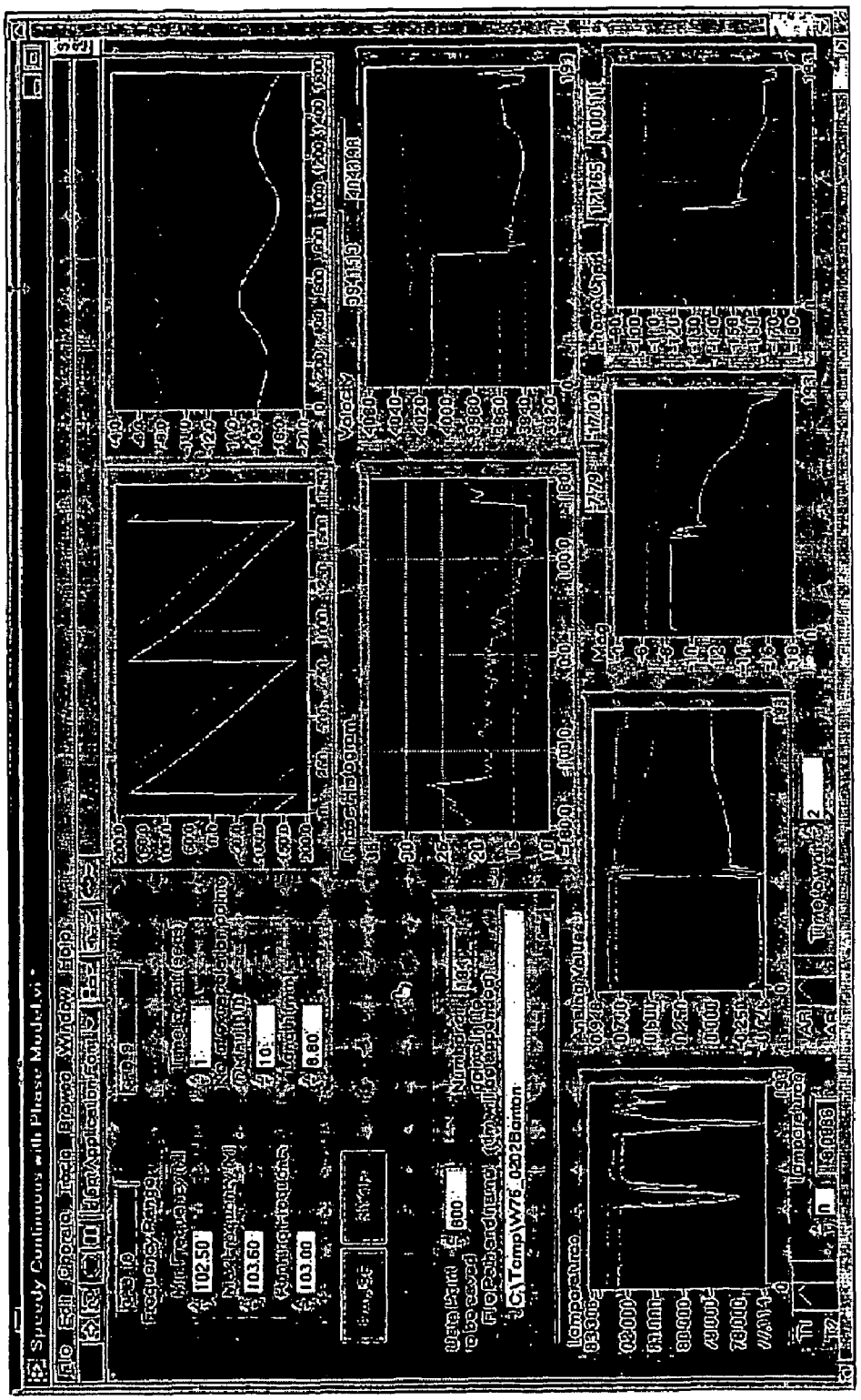
FIG. 5 is a depiction of an exemplary LabView screen associated with execution of the techniques described herein.

LabView was chosen as any easy way to both communicate with the sensor analyzer and to do the calculation based on the model. An exemplary LabView screen associated with execution of the techniques described herein is shown in FIG. 5. The inputs are in part defined by the spectral resolution of the sensor analyzer and include the minimum and maximum frequency (equal to a total of 1600 data points on the sensor analyzer) and the running frequency.

The outputs from LabView allow various interpretations of the results to be made. For the majority of the plots shown on the LabView screen shown there are two outputs, one representing the measurement sensor and the other representing the reference sensor. In LabView, plots of phase and velocity can be used to determine if a sensor is working reliably. If the phase becomes noisy or if the amplitude decreases more than about 20 db then the sensor is deemed bad and discarded.

The phase histogram plot can be used as another measure of sensor quality and relates to non-linearity in the phase plot. The velocity plot may provide the result of the estimation according to the techniques described herein.

Plots of magnitude and phase are taken at the running frequency and plotted against time. Lastly, temperature and analog values are outputs that are plotted against time. In order to calculate velocity from a proper segment of phase frequency response an internal sub-VI is used within LabView. The first step is to calculate all the +180 and −180 degree phase points. In other words, to determine the phase inflection frequencies, the technique may sample a plurality of phase responses at frequencies proximate to the running frequency and estimate the phase inflection frequencies as a function of the plurality of phase responses.

Figure 6:
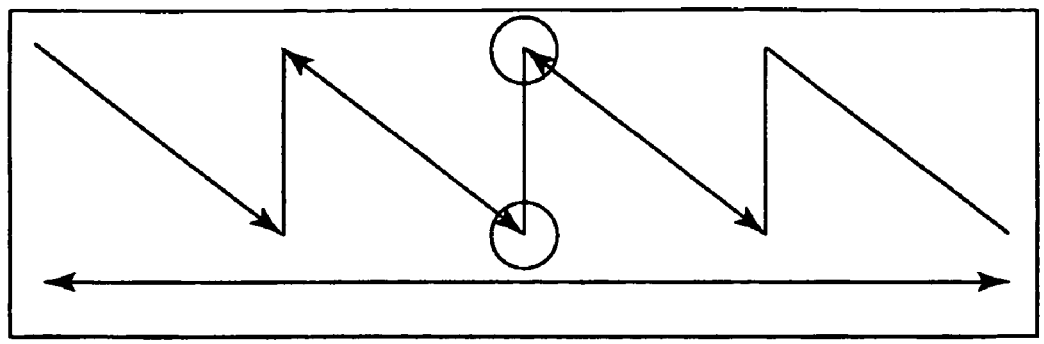
FIG. 6-31 are various graphs illustrating techniques that can be used in accordance with the invention, and various desirable characteristics that can be observed relative to the characteristics observed by conventional techniques.
Figure 7:
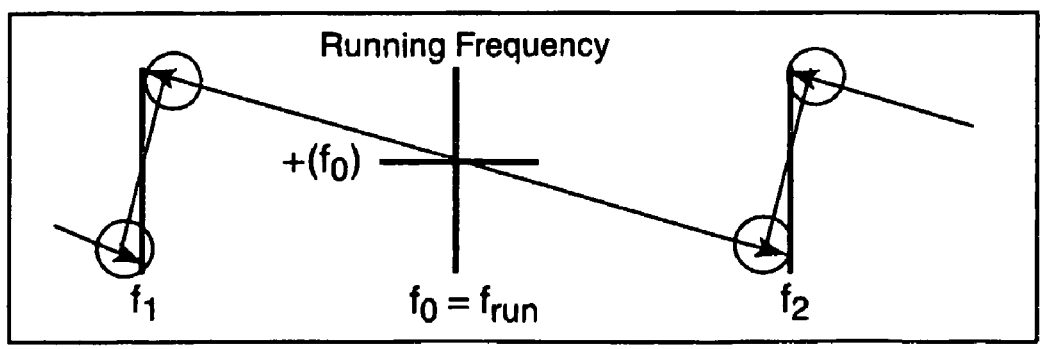

The difference between the velocity expression in continuous frequency and its discrete realization was discussed above. However, this first step may also be applied during the implementation of Algorithm 1 in LabView. For example, if the sensor analyzer has a limited resolution in frequency, the data about a −180 to 180 degree phase transition may be similar to that below:

−175.97, −176.866, −177.761, −178.657, −179.552, 179.5522, 178.6567, 177.7612, 176.8657, 175.9701,

An extrapolated linear fit may be used to find the exact −180 and 180 degree phase points. An illustration of exemplary +180 and −180 degree phase points is shown in FIG. 6. FIG. 7 illustrates use of a bilaterally extrapolated linear fit to find the exact −180 and 180 degree phase. As can be appreciated from FIG. 7 it is possible to calculate the values of $f_1$, $f_2$ and the phase at the running frequency $\phi(f_0)$. However, because the format is different in LabView it may be necessary to use different nomenclature from the model derived above. For example, in LabView:

Tau_Fr=(((F1/(F2−F1))*360)−Pha_Fr+180)/F_13
  run*1000000*360) (with F_run converted to hertz), and then, V_Fr=(L*0.001)/Tau_Fr (with L converted from millimeters to meters). The final output of velocity (V_Fr) is plotted in LabView and corresponds to $\hat{v}(f_0)$, discussed above.

Using a separate application of LabView, it is possible; to take stored phase files and reconstruct velocity data. The phase data can then be transformed using exactly the same model as above. In this way, it is possible to see the effect of changing the running frequency relative to the velocity obtained. LabView allows two ruining frequencies (at 0.1 MHz difference) to be evaluated simultaneously. Advantageously, the phase inflection frequencies define edges of a monotonically changing subset of a graph of phase versus frequency of the surface acoustic wave sensor. Thus, the techniques described herein may allow not only for the identification of a material via the sensor, but also an indication of the concentration of the material.

Example 1

Figure 8:
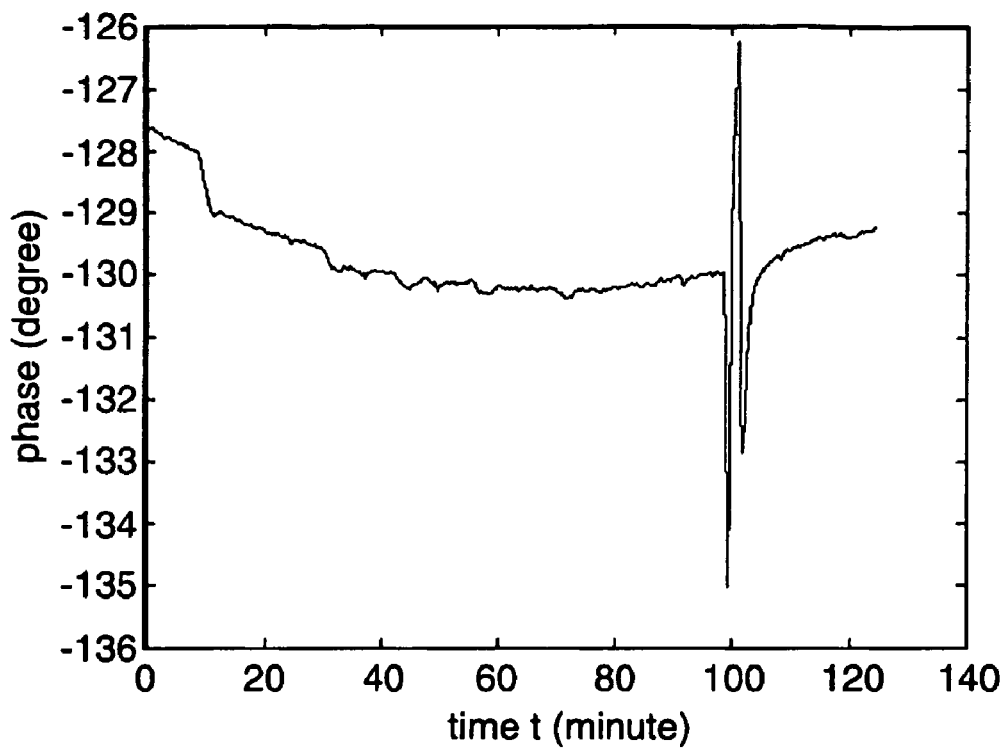
Figure 9:
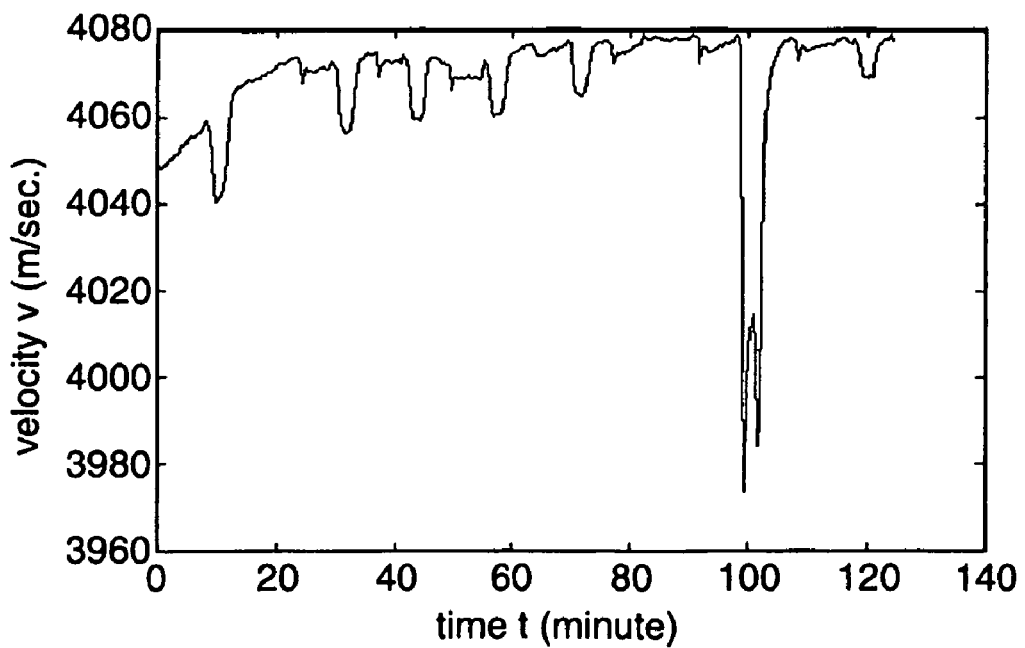

The Love mode SH-SAW sensor used in the experiment was a $LiTaO_3$ device operating at 103 MHz provided by Sandia National Laboratories, USA. A low-walled flow cell was placed over the sensor and filled with Phosphate Buffered Saline (PBS) buffer solution at pH 7.5. This liquid container was connected to a syringe pump system to allow a slow flow of buffer. During the experiment, multiple aliquots of 250 microliters of 0.05 mg/ml Bovine Serum Albumin % (BSA) protein was injected into the cell at designated times. An 8753ET network analyzer from Agilent Technologies, Inc., USA, measured the log-amplitude and phase response of the sensor approximately every twenty seconds. Based on the resulting phase responses, the curve of phase at the operation frequency versus time was immediately obtained. Algorithm 1 was then used to calculate the propagation velocity versus time at the operating frequency. FIGS. 8 and 9 respectively show the phase response and propagation velocity plotted over the time of the experiment. The valleys of the curve of velocity versus time precisely correspond to moments when BSA was injected into the very slowly flowing buffer stream. Compared with the curve of phase versus time, the calculation of propagation velocity provides much more information about the mass loading on the surface of a Love mode SH-SAW sensor, resulting in an increase in sensitivity to mass loading and viscosity.

Example 2

Figure 10:
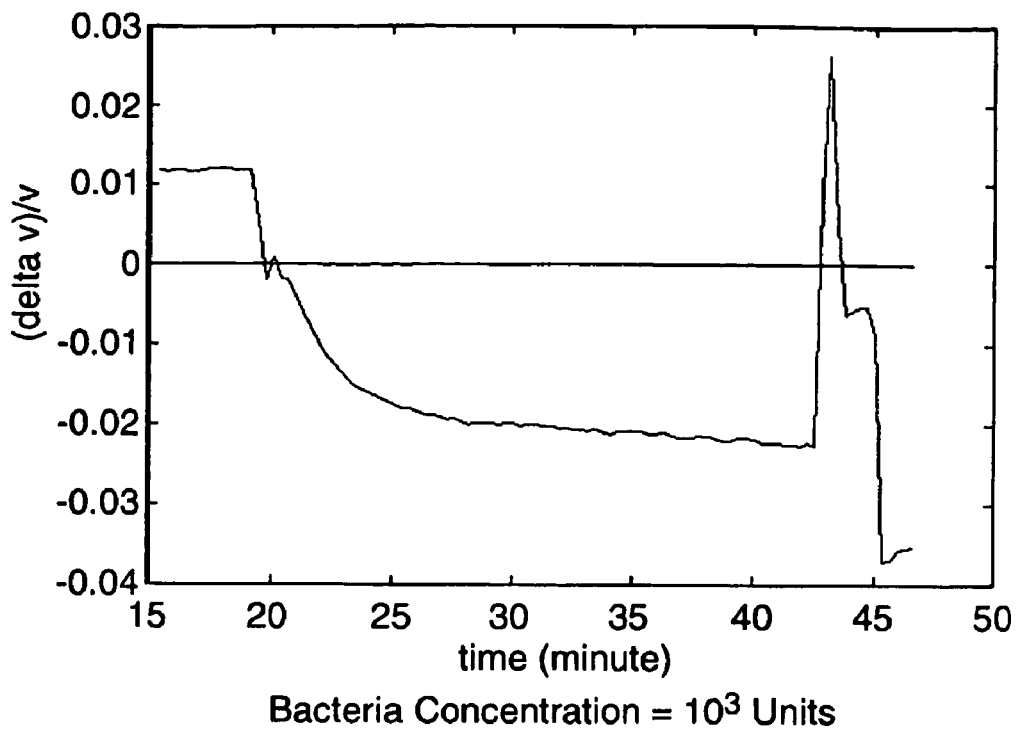
Figure 11:
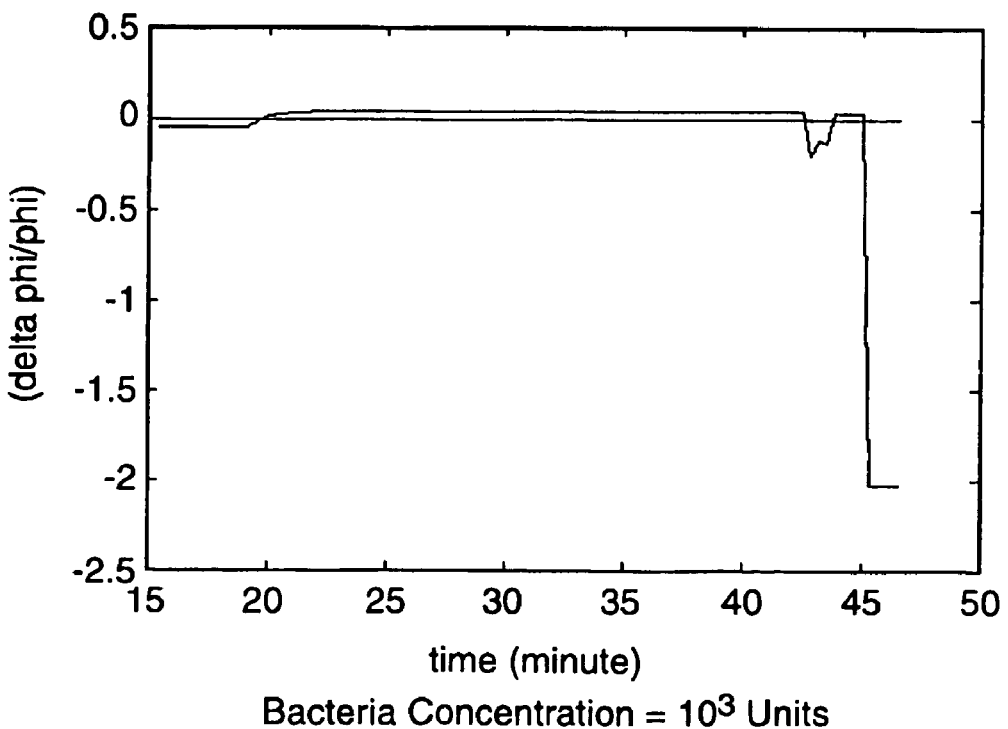
Figure 12:
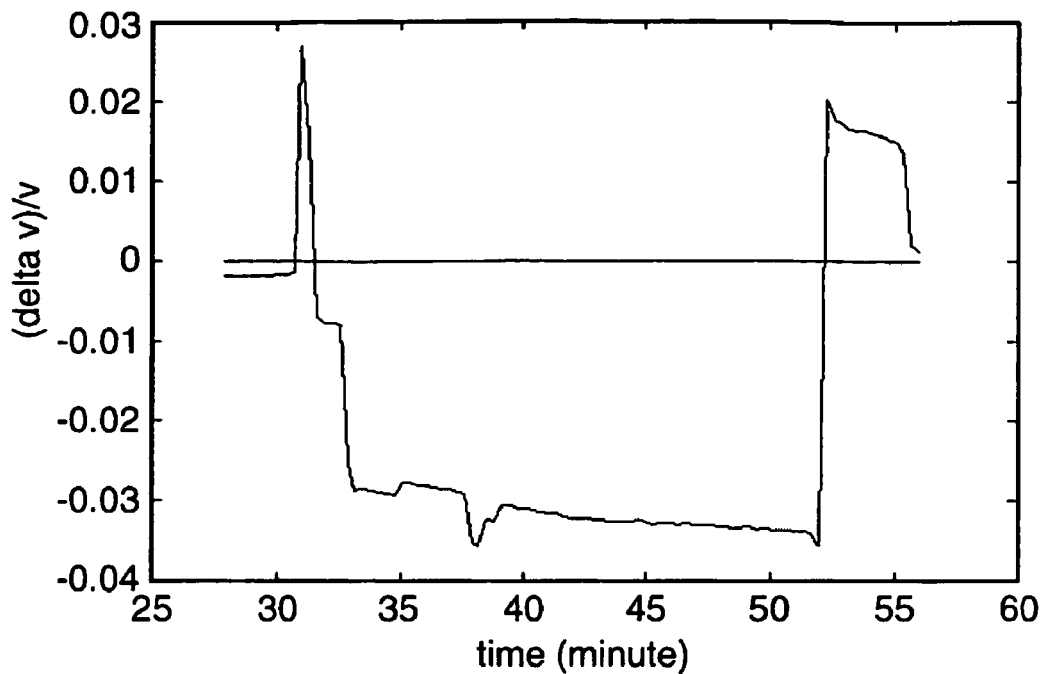
Figure 13:
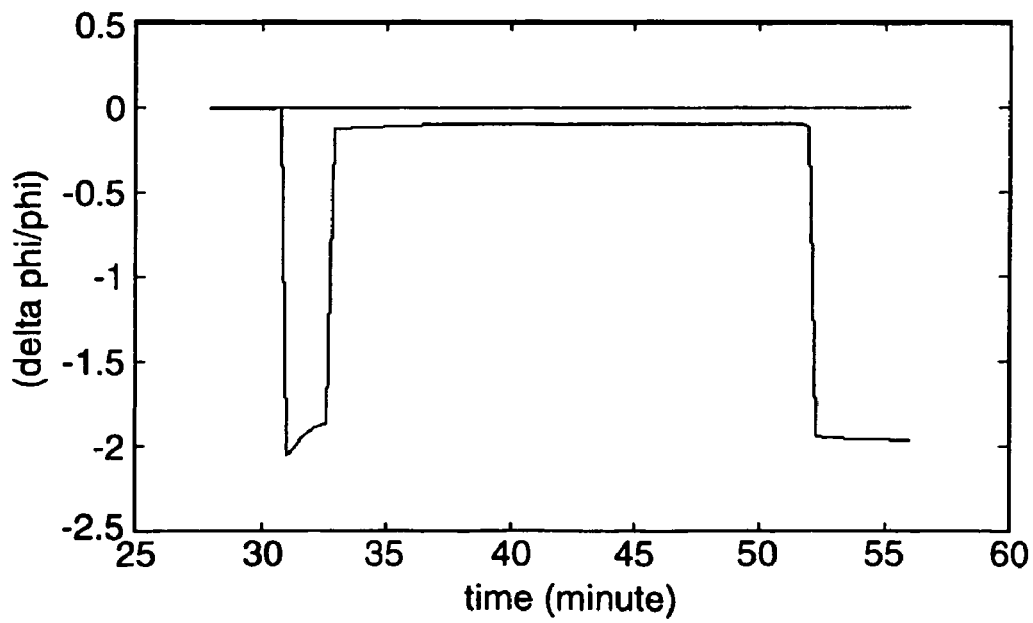

In this example, three separate concentrations of bacteria being detected were used. The first bacterial concentration was $10^3$ cfu/ml (colony forming unit per milliliter), and the results are illustrated in FIGS. 10 and 11. The second bacterial concentration was $10^5$ cfu/ml and the results are illustrated in FIGS. 12 and 13. The third bacterial concentration was $10^7$ cfu/ml and the results are illustrated in FIGS. 14 and 15.

Figure 14:
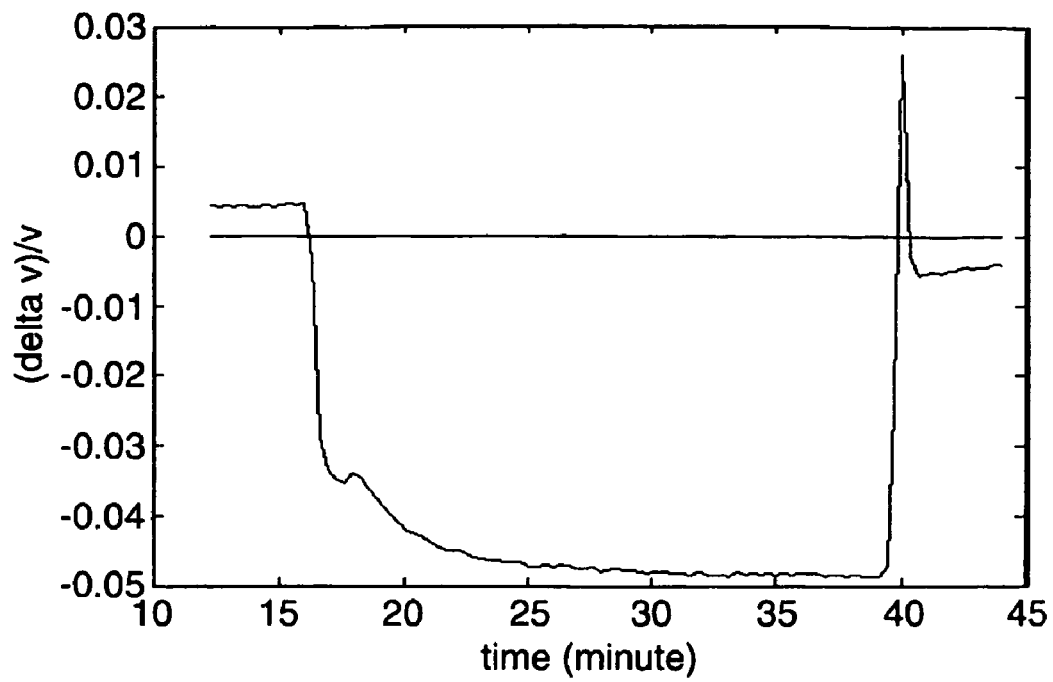
Figure 15:
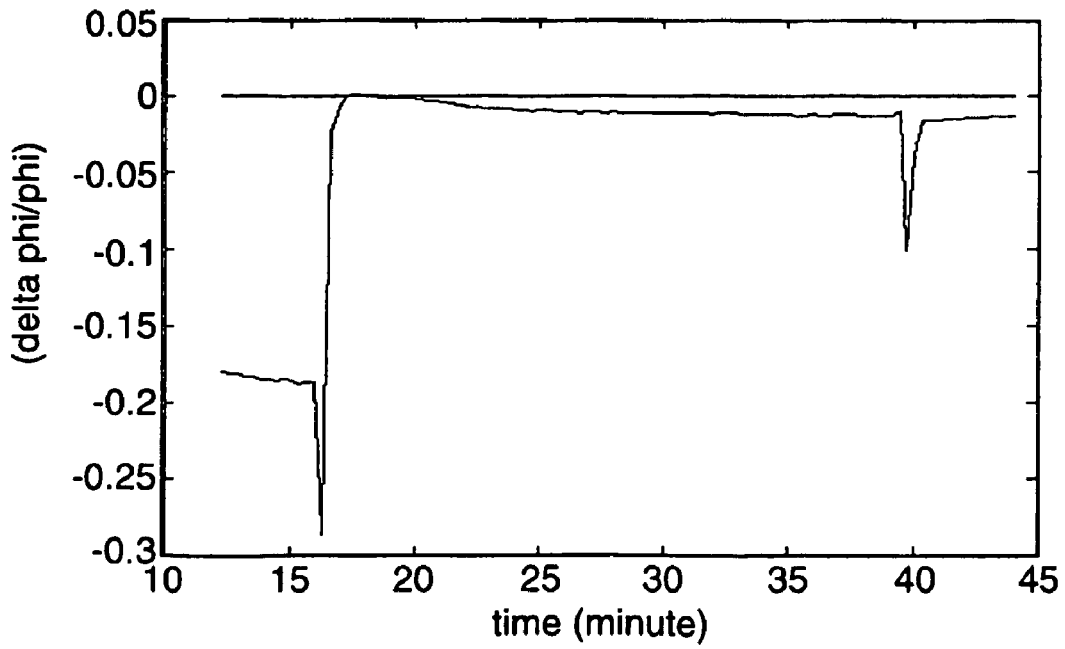

In particular, the graphs of FIGS. 10, 12 and 14 show $\Delta v/v_0$ versus time at the specified concentrations, and the graphs of FIGS. 11, 13 and 15 show $\Delta\phi/\phi_0$ versus time respectively at the specified concentrations. The usual way to use an SH-SAW sensor for mass-loading measurement is that the sensor contains two channels: reference channel and detection channel (the detection channel also being referred to herein as the "active channel" or "active portion" of the sensor). In the reference channel, the surface of the sensor is largely unperturbed, while it is perturbed in the detection channel. By measuring and comparing the propagation characteristics of the two channels, the perturbation resulting from the mass-loading in the detection channel can be detected. If the indicator function, which can be used to describe the difference of the propagation characteristic of the two channels, is monotonic with respect to the mass of the loading material, then the existence of loading mass can be detected and quantified. It has been pointed out above that using $\Delta v/v_0$ as indicator function for detection is better than using $\Delta\phi/\phi_0$ This example demonstrates the correctness of this conclusion from a real experiment. In this experiment, the surface of the detection channel was provided with bacterial loading at specific concentration. The concentrations of the bacteria used in the experiment are $10^3$, $10^5$, and $10^7$ cfu/mL, respectively. The delay from injecting bacteria into the detection channel until back-washing was around 20 minutes. The curves of $\Delta v/v_0$ and $\Delta\phi/\phi_0$ versus time for each bacterial concentration are shown in FIGS. 10-15, where the calculations of the propagation velocities of the two channels are based on the above algorithm. It should be pointed out that the experiment in this example includes no antibody. Bacteria were bound directly to the surface chemistry which was a saccharin immobilization layer.

Figure 16:
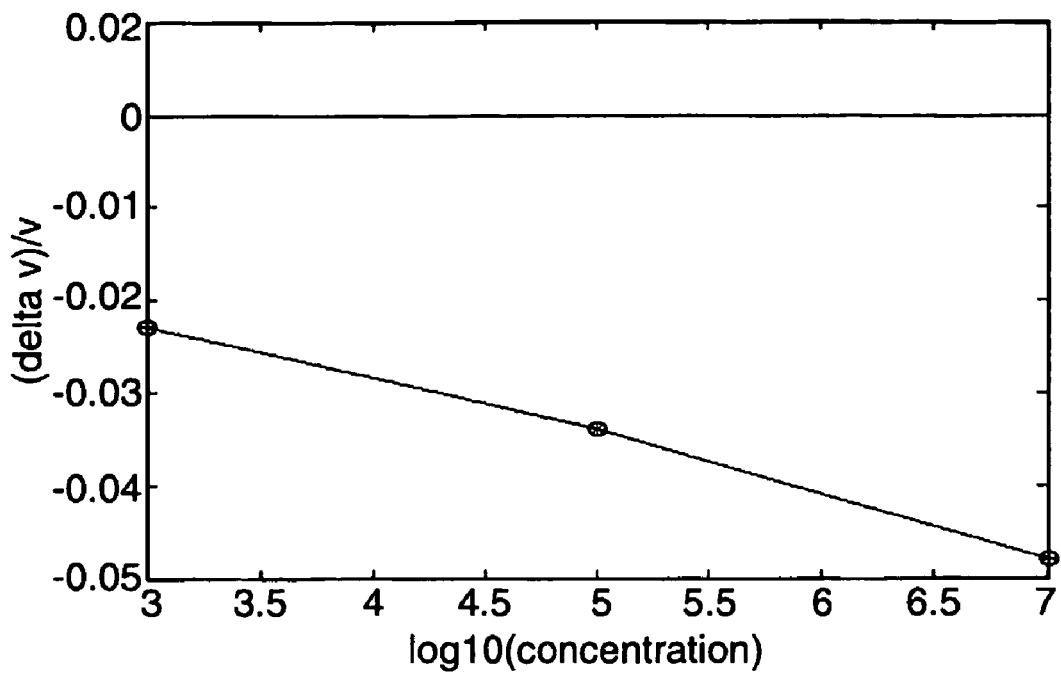
Figure 17:
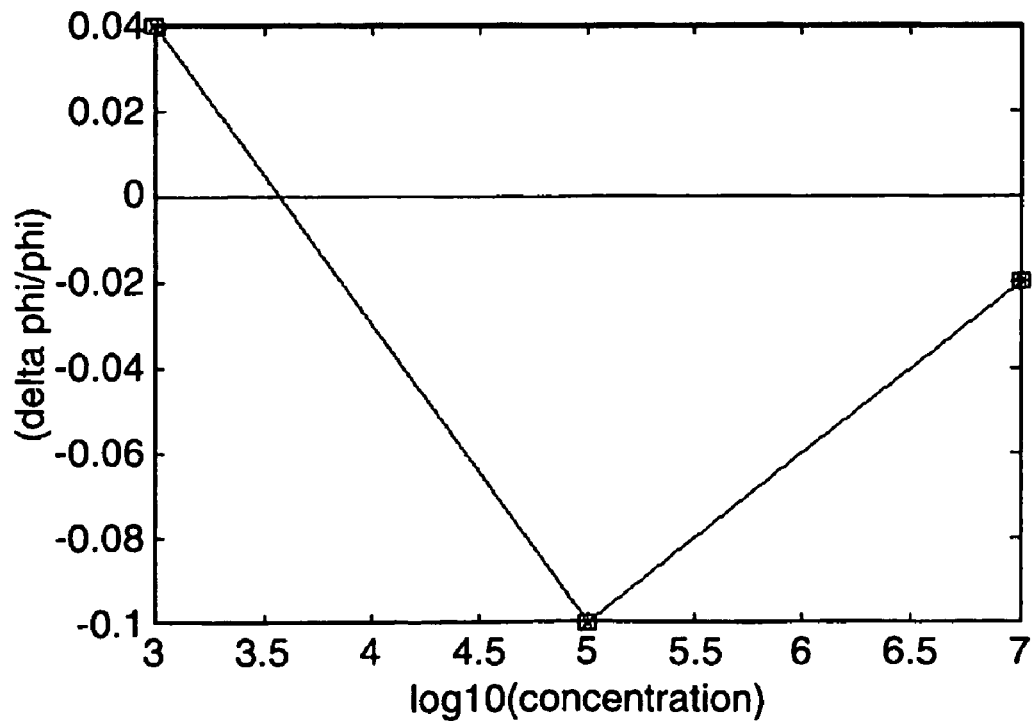

The $\Delta v/v_0$ and $\Delta\phi/\phi_0$ at the steady state are extracted from the above curves for each bacterial concentration. The relationships of $\Delta v/v_0$ versus log-concentration and $\Delta\phi/\phi_0$ versus log-concentration are respectively shown in FIGS. 16 and 17.

Although the experimental results are just for three different bacterial concentrations, clearly, $\Delta\phi/\phi_0$ is not monotonic with respect to the bacterial concentration.

It also demonstrates the correctness of the conclusion that $\Delta\phi/\phi_0$ is not a proper indicator for quantitatively detecting loading mass with large dynamic range.

Example 3

The Love mode SH-SAW sensor used in the experiment was a $LiTaO_3$ device operating at 103 MHz provided by Sandia National Laboratories, USA. During the experiment, the surface of the sensor was:

1. In air for approximately 20 min
2. In buffer for approximately 30 min
3. Subjected to bacteria in the buffer for approximately 18 min
4. Briefly washed and left in buffer for approximately 20 min
5. Subjected to De Ionized (DI) water for approximately 30 min.

Figure 18:
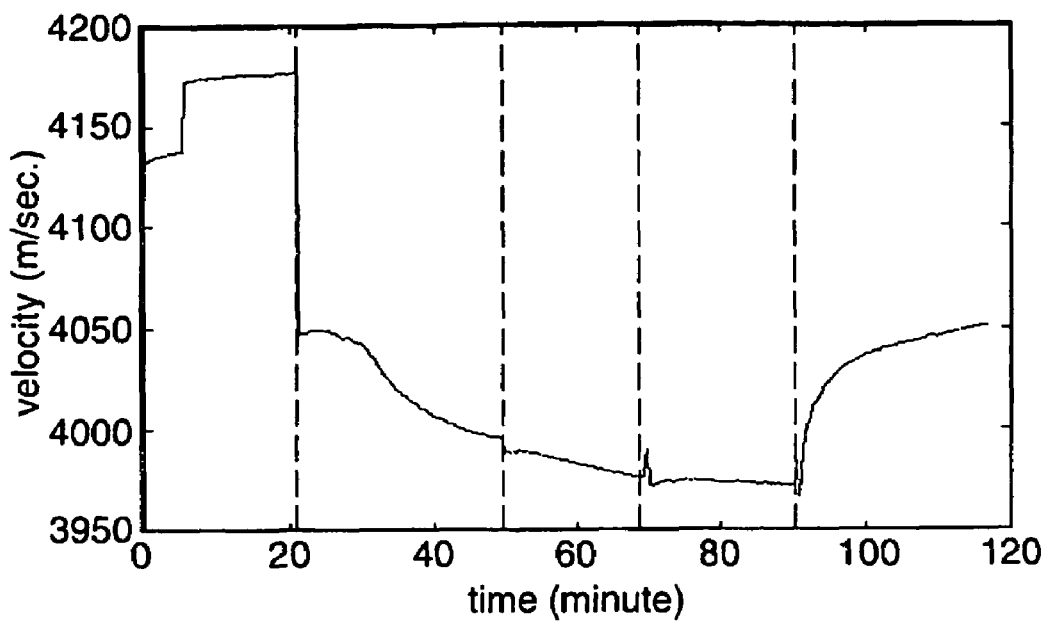
Figure 19:
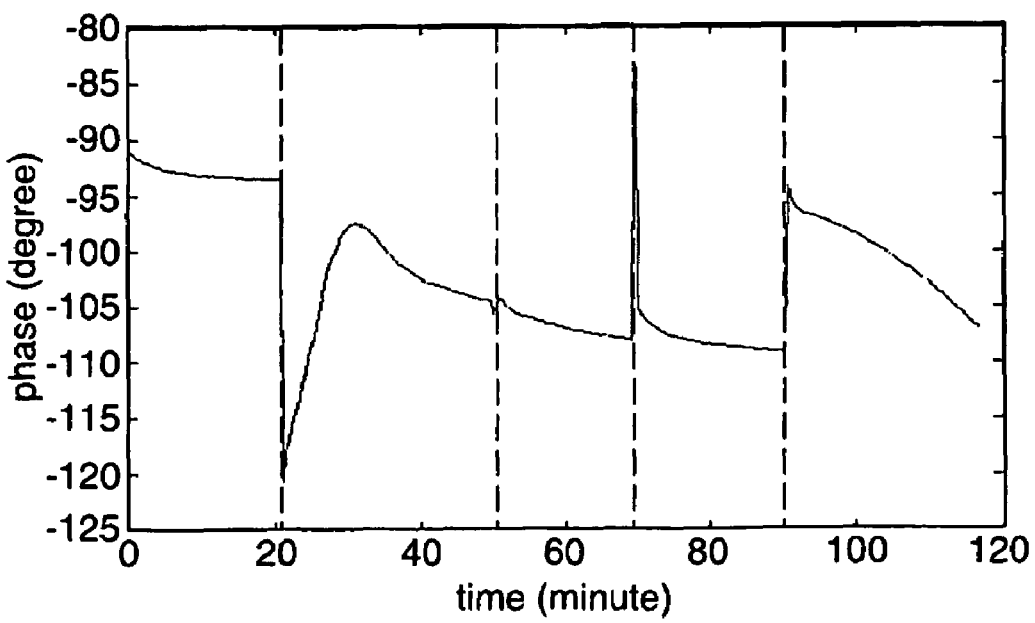

Bacteria were bound to the antibody attached to the surface. FIG. 18 is a graph of the propagation velocity at the operating frequency versus time and FIG. 19 is a graph of phase at the operating frequency versus time. The propagation velocities are calculated using algorithm 1 presented above. In FIGS. 18 and 19, the dashed vertical lines define the time durations of various surface conditions of the sensor as detailed above.

By observing the graph of velocity versus time in FIG. 18, the process and results of the experiment can be understood much more easily. The propagation of the surface acoustic wave of the sensor has higher velocity when its surface was in air as shown at 181. Upon injecting buffer, the velocity decreased and tended to a steady state as shown at 182. Upon adding a certain amount of bacteria, the velocity decreased again as shown at 183. The brief washing did not remove the bacteria, which were adsorbed by the antibody attached to the surface of the sensor. Therefore, the velocity during washing as that in the previous state as shown at 184. Finally, the velocity of the surface acoustic wave sensor increased because the surface condition was changed from the adsorbed bacteria to water as shown at 185. By stark contrast, it is difficult to understand and explain the experimental process and results based on the curve of phase versus time shown in FIG. 19.

Example 4

The Love mode SH-SAW sensor used in the experiment was a $LiTaO_3$ device operating at 103 MHz provided by Sandia National Laboratories, USA. A low-walled flow cell was placed over the sensor and filled with Phosphate Buffered Saline (PBS) buffer solution at pH of approximately 7.5. This liquid container was connected to a syringe pump system to allow a slow flow of buffer. During the experiment, multiple aliquots of 250 microliters of Bovine Serum Albumin (BSA) protein at various concentrations were injected into the cell at designated times. The injection of proteins conformed to Table 1, below. In Table 1, BSA refers to Bovine Serum Albumin, and IgG refers to Immunoglobulin.

TABLE 1

| Injection moment (sampling points in time domain) | Injected Proteins | Concentration (mg/ml) | Age of Solution | Locations of jumping down point of velocity | $\Delta v/v$ |
|---|---|---|---|---|---|
| 70 | BSA | 0.05 | 1 day old | 71 | −0.0193 |
| 96 | IgG | 0.05 | 2 weeks old | | |
| 122 | BSA | 0.05 | 1 day old | 126 | −0.0196 |
| 159 | Buffer | | | | |
| 184 | BSA | 0.05 | 2 weeks old | | |
| 737 | BSA | 0.05 | 1 day old | 741 | −0.0197 |
| 783 | BSA | 0.025 | 1 day old | 787 | −0.0162 |
| 816 | BSA | 0.0125 | 1 day old | 820 | −0.0110 |
| 854 | BSA | 0.0333 | 1 day old | 858 | −0.0169 |
| 888 | BSA | 0.04 | 1 day old | 892 | −0.0186 |
| 916 | BSA | 0.05 | 1 day old | 920 | −0.0201 |
| 948 | BSA | 0.00625 | 1 day old | 952 | −0.0056 |
| 994 | BSA | 0.003125 | 1 day old | 997 | −0.0011 |
| 1023 | BSA | 0.05 | 1 day old | 1027 | −0.0201 |
| 1058 | IgG | 0.05 | 1 day old | 1061 | −0.0014 |
| 1084 | BSA | 0.05 | 1 day old | 1087 | −0.0209 |

Figure 20:
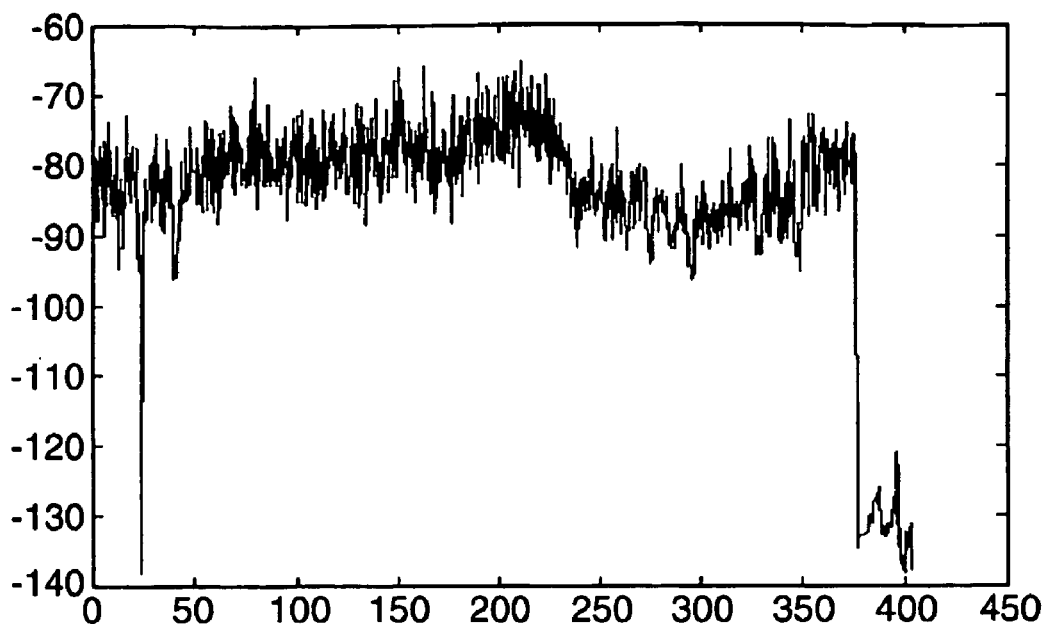
Figure 21:
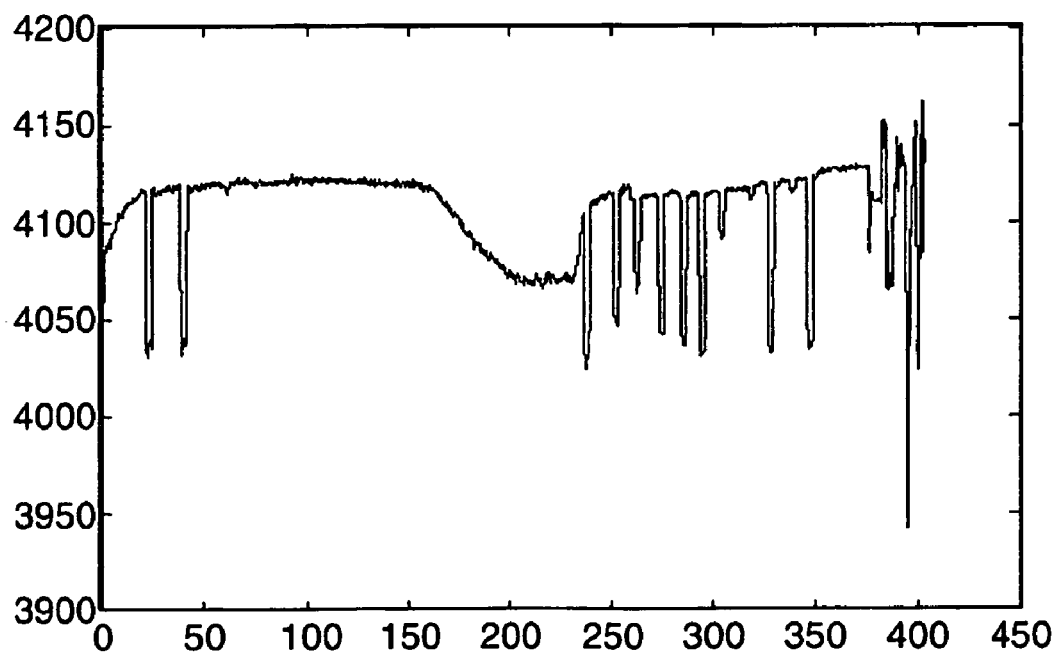

As described in Example 1, an 8753ET network analyzer from Agilent Technologies, Inc., USA, measured the log-amplitude and phase frequency response of the sensor approximately every 20 seconds. Based on proper segments of these phase frequency response for the active channel, and algorithm 1 proposed above, both the curves of phase and propagation velocity at the running frequency versus time fare were obtained. FIG. 20 is the resultant graph of phase versus time, whereas FIG. 21 is the resultant graph of propagation velocity versus time.

Figure 22:
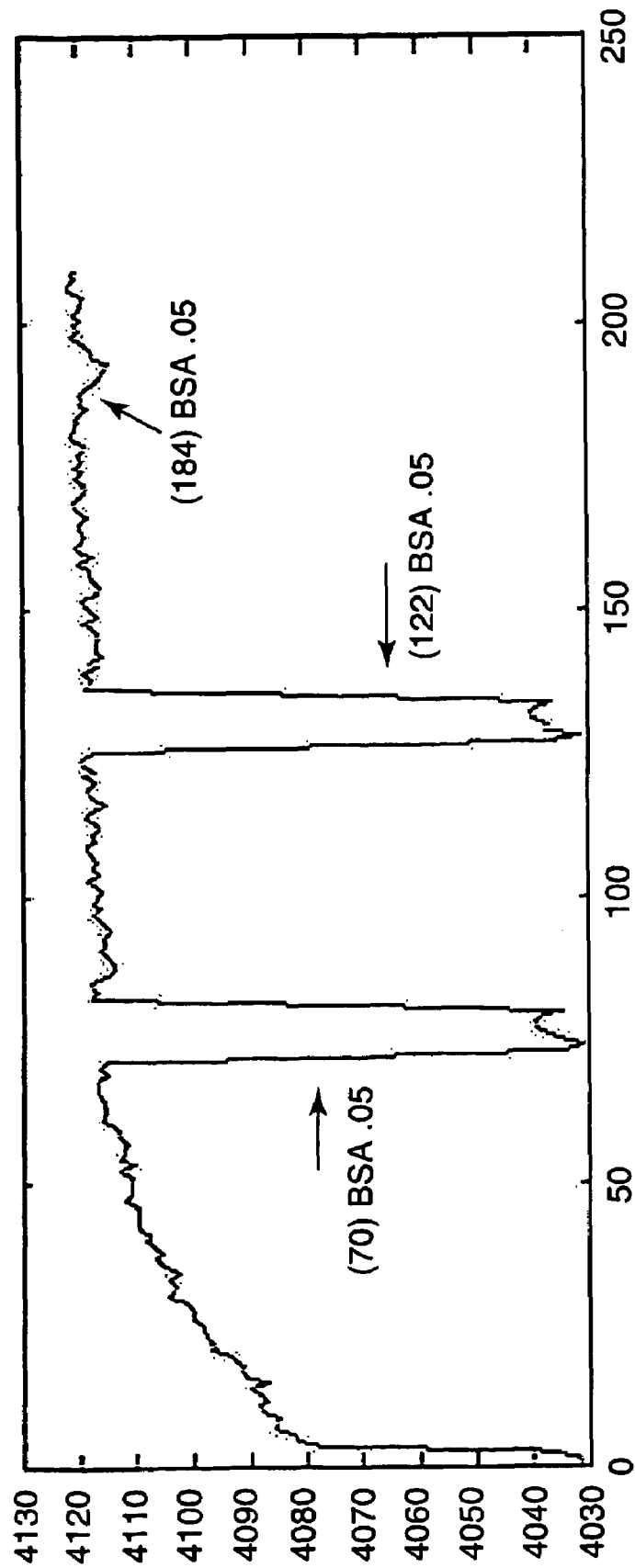
Figure 23:
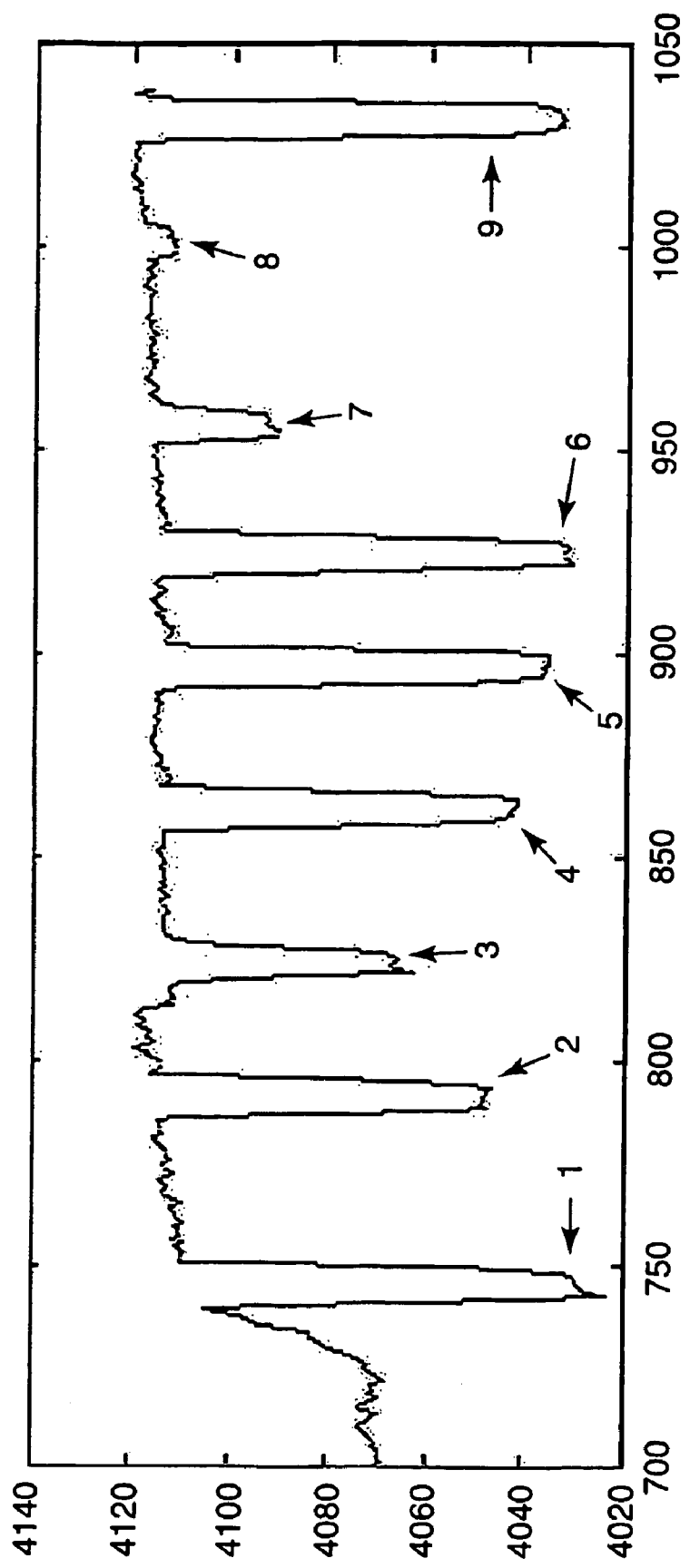
Figure 24:
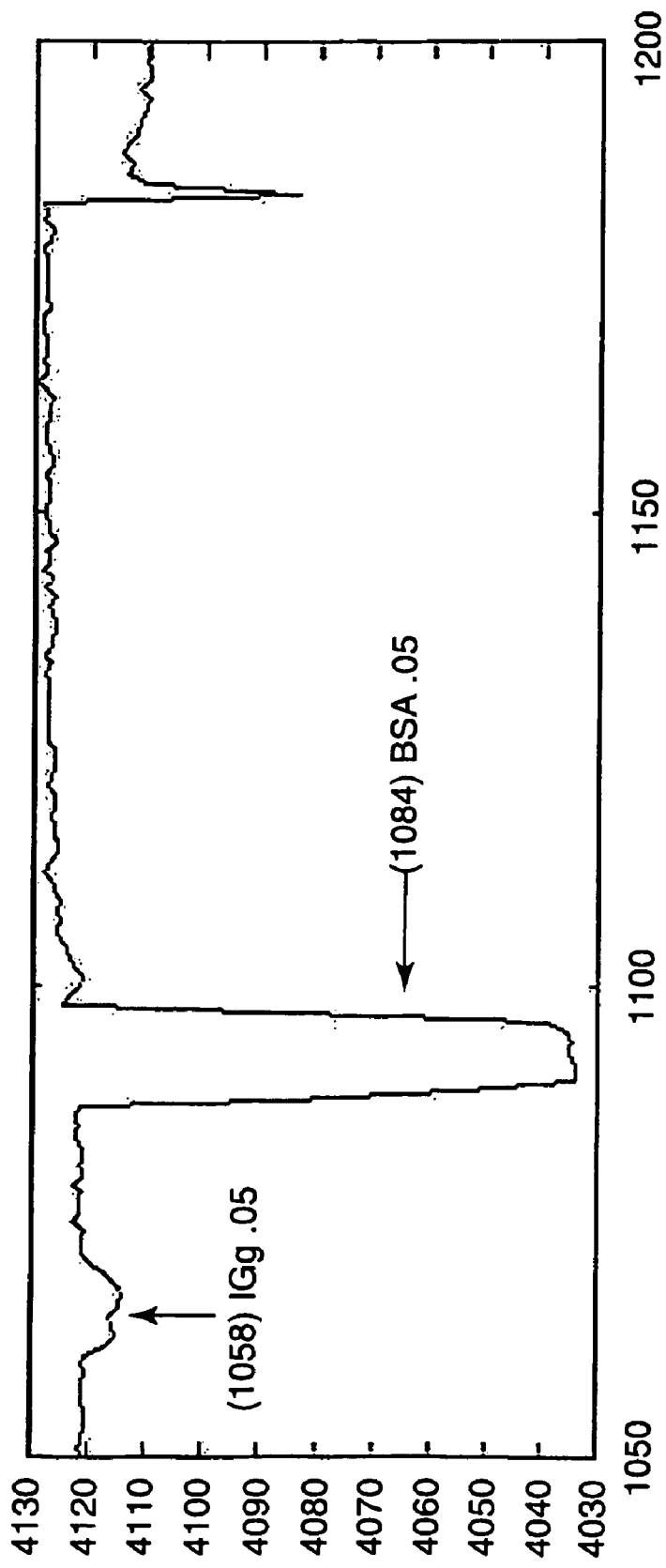
Figure 25:
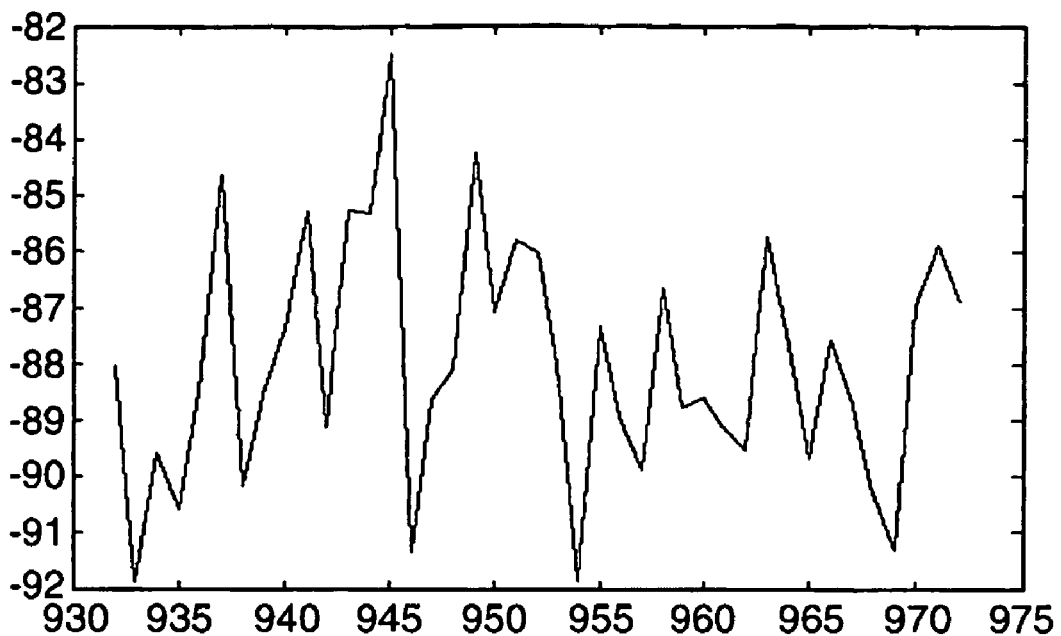
Figure 26:
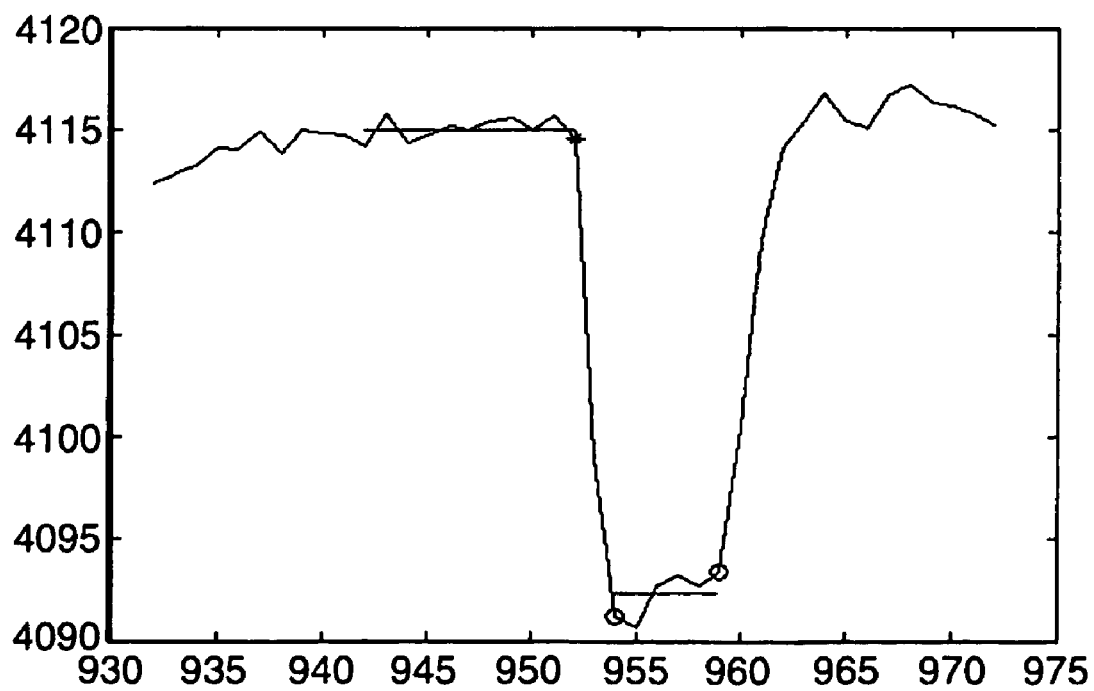

The details of the curve of propagation velocity (m/s) versus time (sampling point in time domain) for BSA injections are shown in the FIGS. 22-24. The locations of the valleys of the curve are very close to the injection moments listed in Table 1. In FIG. 23 the labels correspond to the following:

(1) (737) BSA 0.05 mg/ml;
(2) (783) BSA 0.025 mg/ml;
(3) (816) BSA 0.0125 mg/ml;
(4) (854) BSA 0.0333 mg/ml;
(5) (888) BSA 0.04 mg/ml;
(6) (916) BSA 0.05 mg/ml;
(7) (948) BSA 0.00625 mg/ml;
(8) (994) BSA 0.003125 mg/ml;
(9) (1023) BSA 0.05 mg/ml;

In order to estimate $\Delta v/v$ more accurately, some segments of the curve of velocity around the injection moments of BSA are used. An example is shown in FIG. 26. In this case, the estimated injection moment is the $952^{nd}$ sampling point in time domain. From this segment illustrated in FIG. 26, the edges of the valley are determined and the velocities $v_0$ and $v_1$ are estimated. Then, the $\Delta v/v = (v_1 - v_0)/v_0$ for this injection is calculated, in this case, $\Delta v/v = -0.0056$. FIG. 25 shows the corresponding segment of the curve of $\phi$. It is difficult to determine $\Delta \phi/\phi$ for this injection from the graph of FIG. 25.

Figure 27:
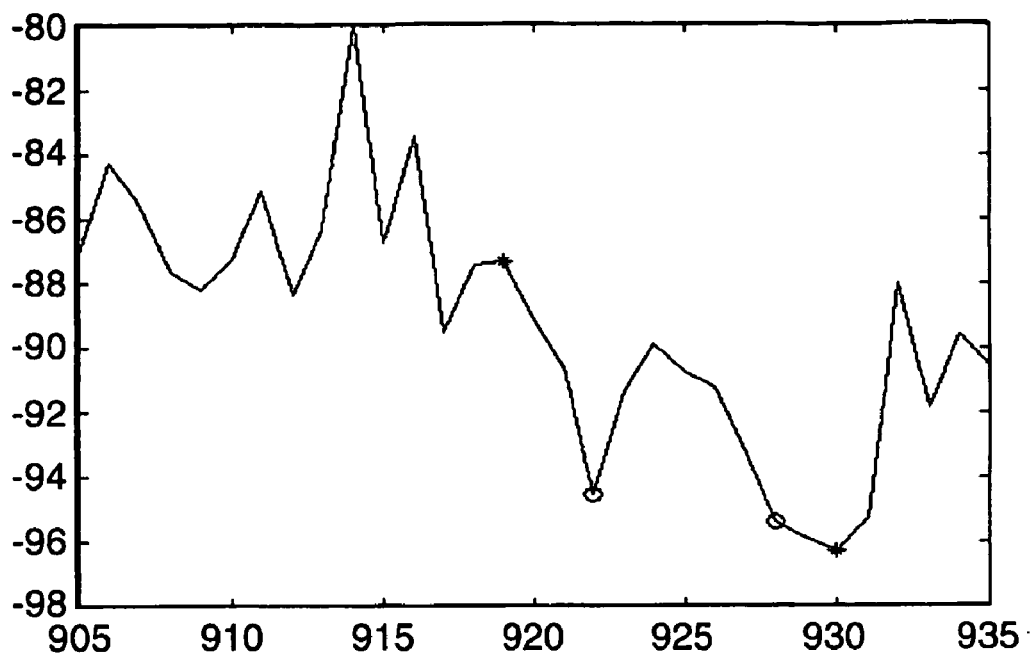
Figure 28:
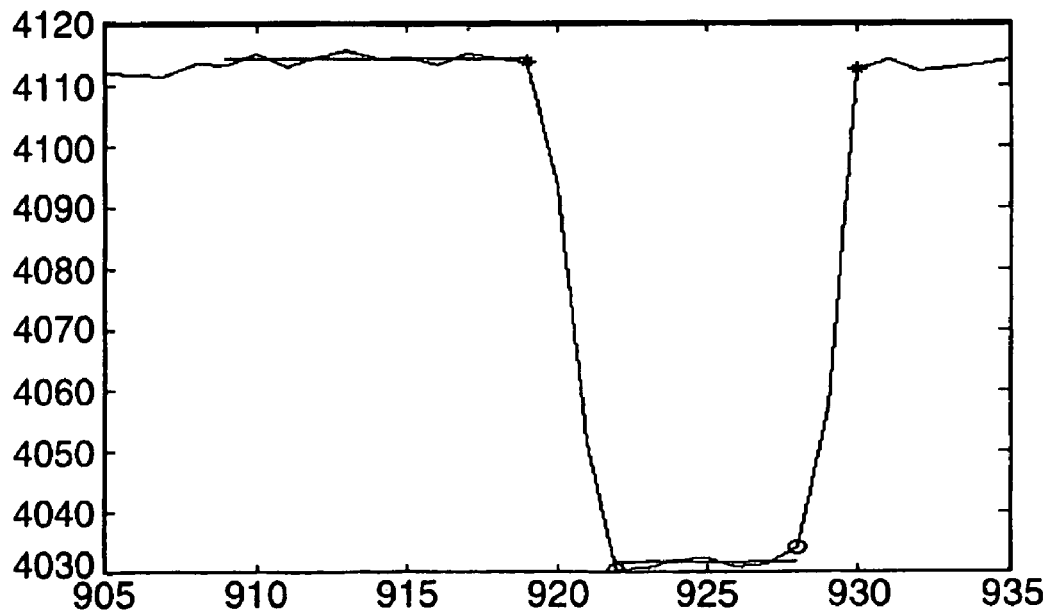
Figure 29:
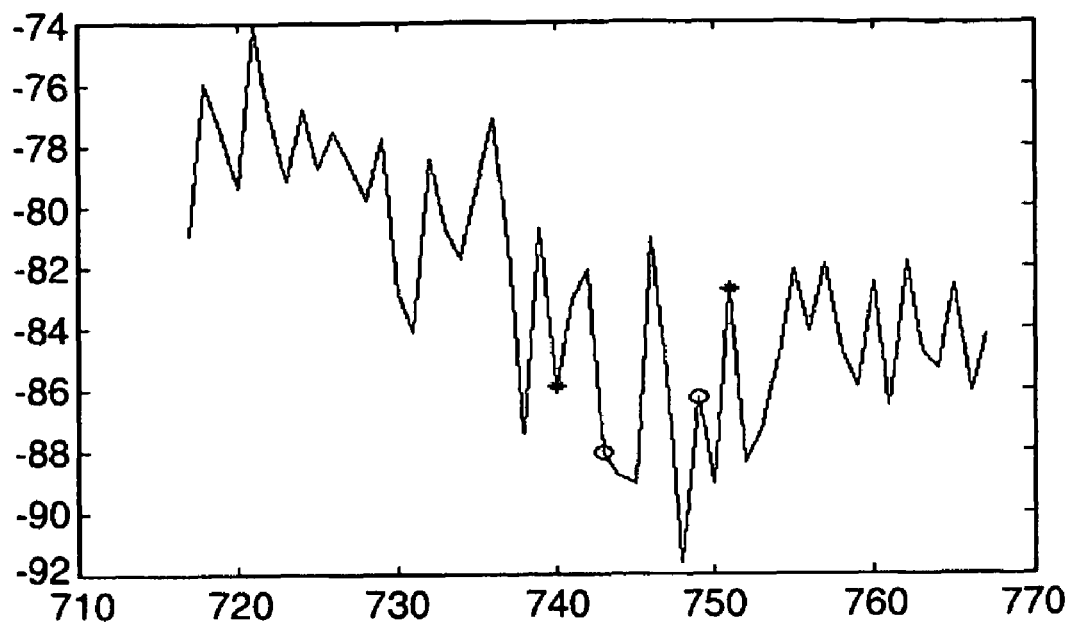
Figure 30:
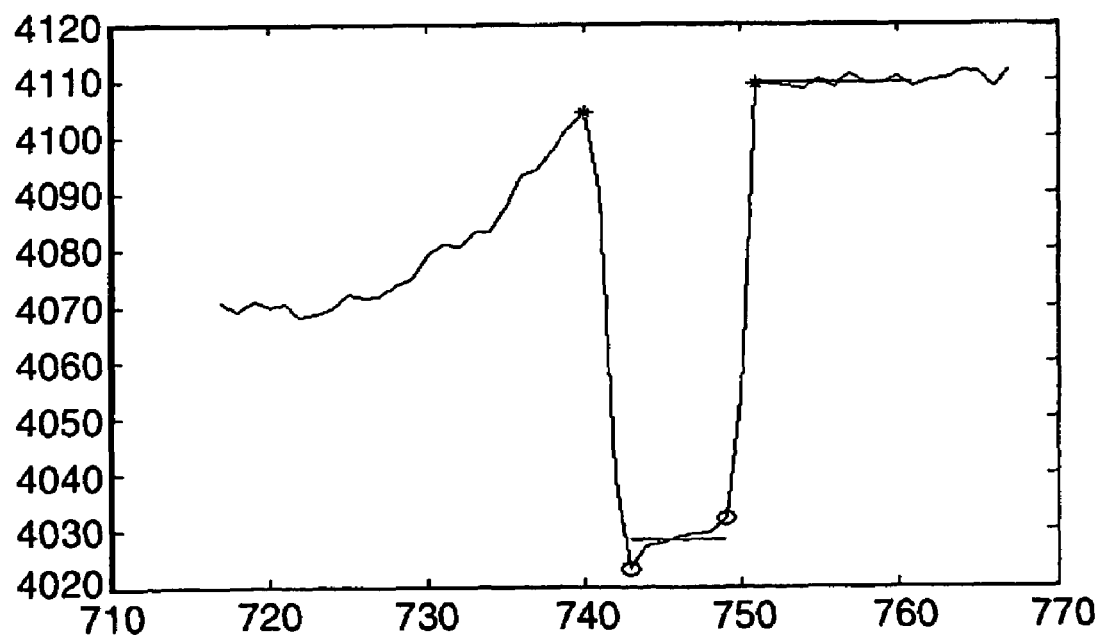

More examples are presented in FIGS. 27-30. In particular, FIGS. 28 and 30 illustrate segments of the curve of v around the estimated injection moments and FIGS. 27 and 29 illustrate the corresponding segments of the curve of $\phi$. The calculated $(\Delta v/v)$'s for FIGS. 28 and 30 are −0.0201 and −0.0197, respectively. It is still difficult to determine $\Delta \phi/\phi$ from FIGS. 27 and 29.

Figure 31:
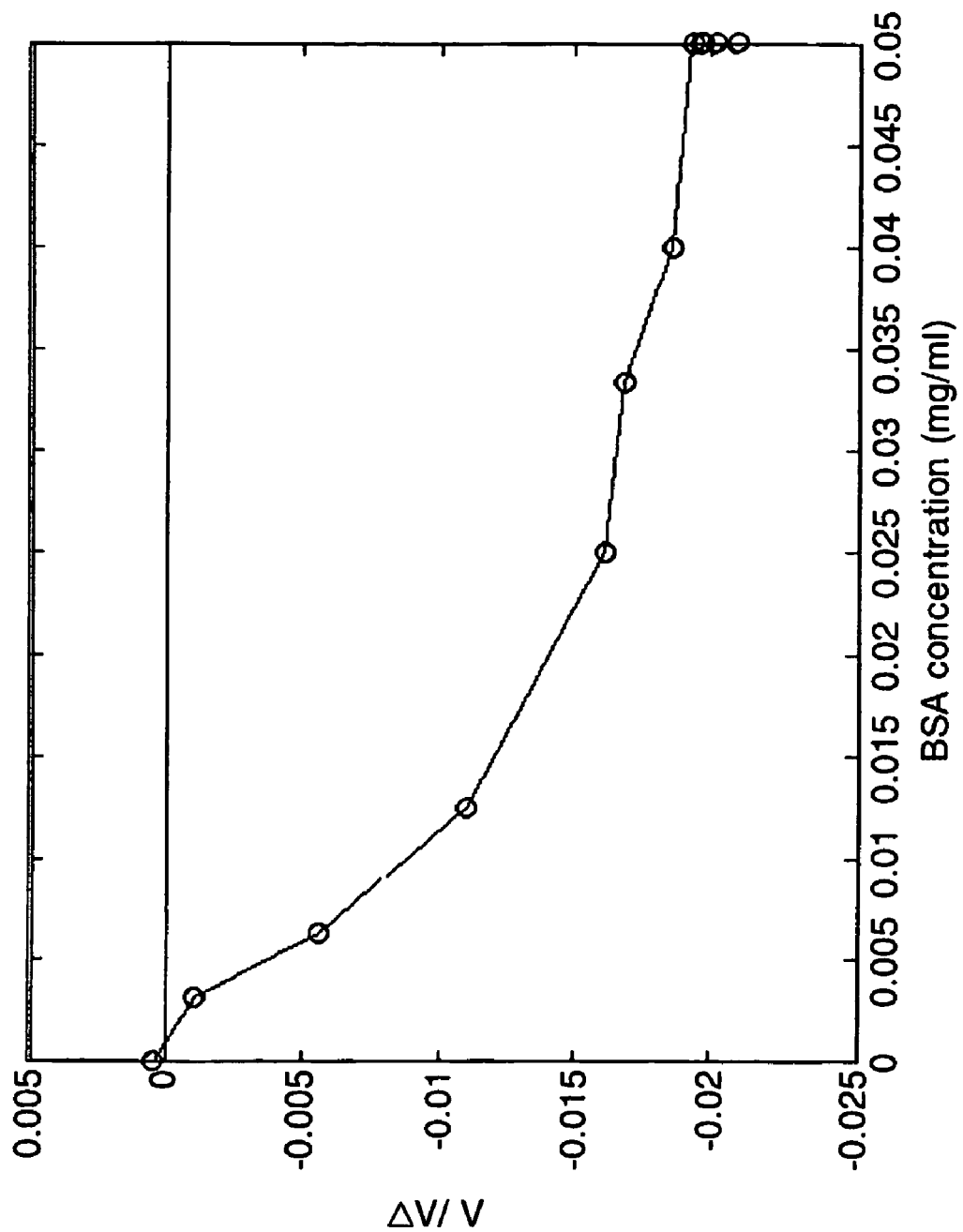

The more accurate estimations of $\Delta v/v$ about the estimated injection moments of BSA are presented in Table 1. The resulting $\Delta v/v$ versus the known concentration of the injected BSA at the same injection moment, which is listed in Table 1, is shown in FIG. 31 as a circle. Corresponding to the concentration 0.05 mg/ml, there are seven overlapping $(\Delta v/v)$'s.

One can examine the circle corresponding to the largest $\Delta v/v$. The curve of FIG. 31 results from connecting the circles. The curve of FIG. 31 is monotonic.

Moreover, the monotonic nature of the curve of FIG. 31 demonstrates that using $\Delta v/v$, which can be determined by the curve of velocity and calibration, the sensor may further detect the concentration of the injected BSA if the concentration of the injected BSA is in the interval [0.003125, 0.05] mg/ml.

The measurement of propagation characteristic of SH-SAW sensor is the base for using the sensor as a detector. The resonance frequency $f_{resonance}$ and propagation velocity v are two direct propagation characteristics and $\Delta v/v$ is more sensitive than $\Delta f/f$ to the surface perturbation. Therefore, the measurement of the propagation velocity is a preferred index for efficiently using SH-SAW sensor as a detector.

In contrast, the conventional approach is to measure the log-amplitude frequency response A(f) and phase frequency response $\phi(f)$ of SH-SAW sensor by a sensor analyzer, and then read out the phase at the running frequency. The serious limitation of $\Delta \phi$ or $\Delta \phi/\phi$ for detection was discussed above. By developing hardware and/or software for the direct measurement of the propagation velocity of the SH-SAW sensor, a practical application of a SH-SAW sensor can be achieved. Based on the system model of SH-SAW sensor with conventional triple transit echo (TTE) techniques, several algorithms have been presented to estimate the propagation velocity from a proper segment of the phase frequency response measured by a sensor analyzer. The first algorithm (algorithm 1) has also been implemented in the software platform LabView for on-line velocity measurement.

Compared with the conventional phase-based or phase shift-based method, the techniques described herein will not lose any information carried by phase. Also, because of overcoming the phase ambiguity, the techniques described herein can extract much more information about the surface condition of SH-SAW sensor relative to conventional techniques. Furthermore, the examples showed the monotonic nature of the curve of $\Delta v/v$ versus concentration of the liquid mass loading in a large dynamic range of the concentration. This may therefore be the basis for using SH-SAW sensor in practice to quantitatively detect mass loading. In contrast, for the curve of $\Delta \phi/\phi$ versus concentration of the liquid mass loading, monotonic curves only hold true for small concentrations.

Various embodiments of the invention have been described. In particular, techniques for estimating the propagation velocity through a surface acoustic wave sensor have been described. The techniques may be implemented in hardware, software, firmware, or the like. Example hardware implementations include implementations within a general purpose microprocessor, an application specific integrated circuit (ASIC), a field programmable gate array (FPGA), specifically designed hardware components, or any combination thereof. In addition, one or more of the techniques described herein may be partially or wholly executed in software. In that case, a computer-readable medium may store or otherwise comprise computer-readable instructions, i.e., program code, that can be executed by a processor or to carry out one of more of the techniques described above. The techniques can be used for both constant time delay (in non-dispersive case) and frequency dependant time delay (in dispersive case).

For example, the computer-readable medium may comprise random access memory (RAM), read-only memory (ROM), non-volatile random access memory (NVRAM), electrically erasable programmable read-only memory (EEPROM), flash memory, or the like. These and other embodiments are within the scope of the following claims.

Suitable methods for coating the devices of the present invention include Applicants' Copending Application U.S. Ser. No. 10/607,698, filed Jun. 27, 2003.

The present invention may be utilized in combination with various materials, methods, systems, apparatus, etc. as described in various patents and published patent applications identified below, all of which are incorporated by reference in their respective entireties. They include: U.S. Publication No. 2007/0065490; U.S. Publication No. 2005/0142296; U.S. Pat. No. 7,169,933; U.S. Pat. No. 7,179,923; U.S. Pat. No. 7,361,767; U.S. Pat. No. 7,423,155; U.S. Pat. No. 7,399,609; U.S. Publication No. 2009/0115004; U.S. Publication No. 2005/0153370, titled "Method of Enhancing Signal Detection of Cell-Wall Components of Cells"; U.S. Pat. No. 7,342,082; U.S. Pat. No. 7,402,678; PCT Publication No. WO2005/066621, titled "Surface Acoustic Wave Sensor Assemblies"; PCT Publication No. WO2005/075 973, titled "Acousto-Mechanical Detection Systems and Methods of Use"; PCT Publication No. WO2005/064349, titled "Detection Cartridges, Modules, Systems and Methods"; and PCT Publication No. WO2005/066092, titled "Acoustic Sensors and Methods".

The complete disclosures of the patents, patent applications, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

The invention claimed is:

1. A method comprising:
   bringing a fluid into contact with the surface of a surface acoustic wave sensor;
   propagating input waves through the surface acoustic wave sensor to produce transmitted waves;
   determining a phase frequency response of the transmitted waves; identifying a segment of phase frequency response by determining first and second phase inflection frequencies, at +180 and −180 degree phase points, proximate to a running frequency associated with the surface acoustic wave sensor;
   estimating a time delay associated with wave propagation through the surface acoustic wave sensor based on the identified segment of phase frequency response;
   identifying a material in the fluid as a function of an estimated propagation velocity, the estimated propagation velocity being estimated based on the estimated time delay.

2. The method of claim 1, wherein the surface acoustic wave sensor comprises a Love mode shear-horizontal surface acoustic wave sensor.

3. The method of claim 1, wherein determining phase inflection frequencies comprises:
   sampling a plurality of phase responses at frequencies proximate to the running frequency and initially estimating phase inflection frequencies as a function of the plurality of phase responses at frequencies proximate to the running frequency;
   sampling a plurality of phase responses at frequencies proximate to the initially estimated phase inflection frequencies; and
   more accurately estimating the phase inflection frequencies as a function of the plurality of phase responses at frequencies proximate to the initially estimated phase inflection frequencies.

4. The method of claim 1, wherein the first and second phase inflection frequencies define edges of a monotonically changing subset of a graph of phase versus frequency of the surface acoustic wave sensor.

5. The method of claim 1 further comprising:
   estimating the time delay associated with wave propagation through the surface acoustic wave sensor based on the identified segment of phase frequency response according to approximately the following equation:

$$\hat{\tau}(f_0) = \frac{f_1}{f_0} \frac{1}{f_2 - f_1} - \frac{1}{360} \frac{\phi(f_0)}{f_0} + \frac{0.5}{f_0}$$

where $\hat{\tau}(f_0)$ is the time delay at frequency $f_0$, $f_0$ is the running frequency, $f_1$ is the first phase inflection frequency, $f_2$, is the second phase inflection frequency, and $\phi(f_0)$ is a measured phase response of the surface acoustic wave sensor at frequency $f_0$.

6. The method of claim 1, further comprising estimating the time delay according to approximately the following equation:

$$\hat{\tau}(f_0) = -\frac{1}{360} \frac{f_*}{f_0} \dot{\phi}(f_*) - \frac{1}{360} \frac{1}{f_0} \phi(f_0) + \frac{1}{360} \frac{1}{f_0} \phi(f_*)$$

where $\hat{\tau}(f_0)$ is the time delay, $f_0$ is the running frequency, $\phi(f_0)$ is a measured phase response of the surface acoustic wave sensor, $f_*$ is any frequency between a first phase inflection frequency and a second phase inflection frequency, $\phi(f_*)$ is a measured phase frequency response at the frequency $f_*$, and $\dot{\phi}(f_*)$ is a first order of derivative of the measured phase response at the frequency $f_*$.

7. The method of claim 1, further comprising estimating the time delay according to approximately the following equation:

$$\hat{\tau} = (f_0) = -\frac{1}{360} \dot{\phi}(f_0)$$

where $\hat{\tau}(f_0)$ is the time delay, and $\dot{\phi}(f_0)$ is a first order of derivative of a measured phase response at a frequency $f_0$.

8. The method of claim 1, further comprising estimating the time delay according to approximately the following equation:

$$\hat{\tau}(f_0) = \frac{1}{f_0}\frac{f_1}{f_2-f_1} - \frac{1}{360}\frac{1}{f_0}\phi(f_0) + \frac{0.5}{f_0} + \frac{1}{180}\frac{1}{f_0}\frac{1}{f_2-f_1}\int_{f_1}^{f_2}\phi(f_{00})\,df_{00}$$

where $\hat{\tau}(f_0)$ is the time delay, $f_0$ is the running frequency, $f_1$ is the first phase inflection frequency, $f_2$ is the second phase inflection frequency, and $\phi(f_0)$ is a measured phase response of the surface acoustic wave sensor, integral $$\int_{f_1}^{f_2}\phi(f_{00})\,df_{00}$$

is equal to integral $$\int_{f_1}^{f_2}\phi(f)\,df,$$

where $\phi(f)$ is a measured phase response at frequency f and f varies from $f_1$ to $f_2$.

9. The method of claim 1, further comprising estimating the propagation velocity of a surface acoustic wave through the surface acoustic wave sensor from the estimated time delay according to the following equation:

$$\hat{v}(f) = \frac{L}{\hat{\tau}(f)},$$

where $\hat{v}(f)$ is the estimated propagation velocity of the surface acoustic wave at frequency f, $\hat{\tau}(f)$ is the estimated time delay at the frequency f, and L is a distance between centers of an input inter-digitized transducer (IDT) and an output IDT which are part of the surface acoustic wave sensor.

10. A computer-readable medium comprising instructions that when executed in a processor:
determine phase frequency response of transmitted waves of a surface acoustic wave sensor;
identify a segment of phase frequency response of the surface acoustic wave sensor by determining first and second phase inflection frequencies proximate to a running frequency associated with the surface acoustic wave sensor;
estimate a time delay associated with wave propagation through the surface acoustic wave sensor based on the identified frequency response according to approximately the following equation:

$$\hat{\tau}(f_0) = \frac{f_1}{f_0}\frac{1}{f_2-f_1} - \frac{1}{360}\frac{\phi(f_0)}{f_0} + \frac{0.5}{f_0}$$

where $\hat{\tau}(f_0)$ is the time delay at frequency $f_0$, $f_0$ is the running frequency, $f_1$ is the first phase inflection frequency, $f_2$ is the second phase inflection frequency, and $\phi(f_0)$ is a measured phase response of the surface acoustic wave sensor at the running frequency $f_0$; and
identify a concentration of a material in a fluid as a function of an estimated propagation velocity that is based on the estimated time delay.

11. The computer-readable medium of claim 10, further comprising instructions that when executed determine phase inflection frequencies for a discrete phase frequency response by:
sampling a plurality of phase responses at frequencies proximate to the running frequency and initially estimating phase inflection frequencies as a function of the plurality of phase responses at frequencies proximate to the running frequency; sampling a plurality of phase responses at frequencies proximate to the initially estimated phase inflection frequencies; and
more accurately estimating phase inflection frequencies as a function of the plurality of phase responses at frequencies proximate to the initially estimated phase inflection frequencies.

12. The computer-readable medium of claim 10, wherein the first and second phase inflection frequencies define edges of a monotonically changing subset of a graph of phase versus frequency of the surface acoustic wave sensor.

13. The computer-readable medium of claim 10, further comprising instructions that when executed estimate a propagation velocity of the surface acoustic wave from the estimated time delay according to the following equation:

$$\hat{v}(f) = \frac{L}{\hat{\tau}(f)},$$

where $\hat{v}(f)$ is the estimated propagation velocity of the surface acoustic wave at frequency f, $\hat{\tau}(f)$ is the estimated time delay at frequency f, and L is a distance between centers of an input inter-digitized transducer IDT and an output IDT which are part of the surface acoustic wave sensor.

14. The computer-readable medium of claim 10, wherein the surface acoustic wave sensor comprises a Love mode shear-horizontal surface acoustic wave sensor.

15. A system comprising:
a surface acoustic wave sensor;
a sensor analyzer to receive output of the surface acoustic wave sensor and determine a phase frequency response from the output; and
a processor to receive input from the sensor analyzer, identify a segment of phase frequency response of the surface acoustic wave sensor by determining first and second phase inflection frequencies proximate to a running frequency associated with the surface acoustic wave sensor, estimate a time delay associated with wave propagation through the surface acoustic wave sensor based on the identified segment of phase frequency response according to approximately the following equation:

$$\hat{\tau}(f_0) = \frac{f_1}{f_0}\frac{1}{f_2-f_1} - \frac{1}{360}\frac{\phi(f_0)}{f_0} + \frac{0.5}{f_0}$$

where $\hat{\tau}(f_0)$ is the time delay at frequency $f_0$, $f_0$ is the running frequency, $f_1$ is the first phase inflection frequency, $f_2$ is the second phase inflection frequency, and $\phi(f_0)$ is a measured phase response of the surface acoustic wave sensor at the running frequency $f_0$, estimate a propagation velocity of the surface acoustic wave based on the estimated time delay, and identify a concentration of a material in a fluid as a function of the estimated propagation velocity.

16. The system of claim 15 wherein the processor determines the phase inflection frequencies by:
   sampling a plurality of phase responses at frequencies proximate to the running frequency and initially estimating the phase inflection frequencies as a function of the plurality of phase responses at frequencies proximate to the running frequency;
   sampling a plurality of phase responses at frequencies proximate to the initially estimated phase inflection frequencies; and
   more accurately estimating the phase inflection frequencies as a function of the plurality of phase responses at frequencies proximate to the initially estimated phase inflection frequencies.

17. The system of claim 15 wherein the first and second phase inflection frequencies define edges of a monotonically changing subset of a graph of phase versus frequency of the surface acoustic wave sensor.

18. The system of claim 15, wherein the processor estimates propagation velocity of the surface acoustic wave based on the estimated time delay according to the following equation:

$$\hat{v}(f) = \frac{L}{\hat{\tau}(f)},$$

where $\hat{v}(f)$ is an estimated propagation velocity of the surface acoustic wave at a frequency f, $\hat{\tau}(f)$ is the estimated time delay at the frequency f, and L is a distance between centers of an input inter-digitized transducer IDT and an output IDT which are part of the surface acoustic wave sensor.

19. The system of claim 15, wherein the surface acoustic wave sensor comprises a Love mode shear-horizontal surface acoustic wave sensor.

* * * * *

UNITED STATES PATENT AND TRADEMARK OFFICE
CERTIFICATE OF CORRECTION

PATENT NO. : 7,677,101 B2 Page 1 of 1
APPLICATION NO. : 10/596674
DATED : March 16, 2010
INVENTOR(S) : Wenyuan Xu It is certified that error appears in the above-identified patent and that said Letters Patent is hereby corrected as shown below:

Column 13
Line 48, delete "DITs" and insert -- IDTs --, therefor.

Column 14
Lines 55-56, delete "$F_{13}$ run*" and insert -- F_run* --, therefor.
Line 61, delete "possible;" and insert -- possible --, therefor.
Line 66, delete "ruining" and insert -- running --, therefor.

Column 17
Line 35, delete "response" and insert -- responses --, therefor.

Column 20
Line 35, in Claim 5, delete "$f_2$," and insert -- $f_2$ --, therefor.

Column 22
Line 26, in Claim 13, after "estimate" delete "a".

Signed and Sealed this

Fourth Day of May, 2010

David J. Kappos
*Director of the United States Patent and Trademark Office*